(12) United States Patent
Rigoutsos et al.

(10) Patent No.: US 8,178,503 B2
(45) Date of Patent: *May 15, 2012

(54) RIBONUCLEIC ACID INTERFERENCE MOLECULES AND BINDING SITES DERIVED BY ANALYZING INTERGENIC AND INTRONIC REGIONS OF GENOMES

(75) Inventors: Isidore Rigoutsos, Astoria, NY (US); Tien Huynh, Yorktown Heights, NY (US); Aristotelis Tsirigos, Astoria, NY (US); Alice Carolyn McHardy, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 1657 days.

This patent is subject to a terminal disclaimer.

(21) Appl. No.: 11/408,557

(22) Filed: Apr. 21, 2006

(65) Prior Publication Data

US 2011/0178283 A1    Jul. 21, 2011

Related U.S. Application Data

(63) Continuation-in-part of application No. 11/367,512, filed on Mar. 3, 2006.

(51) Int. Cl.
*C12N 15/11* (2006.01)
(52) U.S. Cl. .................................... 514/44 A
(58) Field of Classification Search .................. 514/44 A
See application file for complete search history.

(56) References Cited

U.S. PATENT DOCUMENTS

| | | | | |
|---|---|---|---|---|
| 8,065,091 B2 * | 11/2011 | Rigoutsos et al. | ............... | 702/19 |
| 2005/0244879 A1 | 11/2005 | Schumm et al. | | |
| 2007/0050146 A1 * | 3/2007 | Bentwich et al. | ............... | 702/19 |

OTHER PUBLICATIONS

Krutzfeldt et al. (Nature Genetics, 2006, 38: S14-S19).*
I. Rigoutsos et al., "Combinatorial Pattern Discovery in Biological Sequences: the Teiresias Algorithm," Bioinformatics 1, Jan. 1998, pp. 55-67, vol. 14, No. 1.
G. Bejerano et al., "Ultraconserved Elements in the Human Genome," Science Magazine, May 2004, pp. 1321-1325, vol. 304.
M. Ashburner et al. "Gene Ontology: Tool for the Unification of Biology, The Gene Ontology Consortium," Nature Genetics, May 2000, pp. 25-29, vol. 25.
S. Iwashita et al., "A Transposable Element-Mediated Gene Divergence that Directly Produces a Novel Type Boeine Bent Protein Including the Endonuclease Domain of RTE-1," Society of Molecular Biology and Evolution, 2003, pp. 1556-1563, vol. 20, No. 9.
G. Lev-Maor et al., "The Birth of an Alternatively Spliced Exon: 3' Splice-Site Selection in Alu Exons," Science Magazine, May 2003, pp. 1288-1291, vol. 300.
N. Jiang et al., "Pack-MULE Transposable Elements Mediate Gene Evolution in Plants," Nature, Sep. 2004, pp. 569-573, vol. 431.
R.A. Jorgensen, "Restructuring the Genome in Response to Adaptive Challenge: McClintock's Bold Conjecture Revisited," Cold Spring Harbor Symposia on Quantitative Biology, 2004, pp. 349-354, vol. LXIX.
J.C. Wootton et al., "Statistics of Local Complexity in Amino Acid Sequences and Sequence Databases," Computers in Chemistry, 1993, pp. 149-163, vol. 17, No. 2.
X. Xie et al., "Systematic Discovery of Regulatory Motifs in Human Promoters and 3' UTRs by Comparison of Several Mammals," Nature, Mar. 2005, pp. 338-345, vol. 434.
R. Chenna et al., "Multiple Sequence Alignment with the Clustal Series of Programs," Nucleic Acids Research, 2003, pp. 3497-3500, vol. 31, No. 13.
A. Stabenau et al., "The Ensembl Core Software Libraries," Genome Research, 2004, pp. 929-933, vol. 14.
S.F. Altschul et al., "Basic Local Alignment Search Tool," J Mol Biol., 1990, pp. 403-410), vol. 215.
I.L. Hofacker et al., "Fast Folding and Comparison of RNA Secondary Structures," Monatshefte fur Chemie, 1994, pp. 167-188, vol. 125.
S. Griffiths-Jones et al., "Rfam: an RNA Family Database," Nucleic Acids Research, 2003, pp. 439-441, vol. 31, No. 1.

* cited by examiner

*Primary Examiner* — Brian Whiteman
(74) *Attorney, Agent, or Firm* — Ryan, Mason & Lewis, LLP

(57) ABSTRACT

In one aspect of the invention, a method for regulating the expression of a transcript comprises using at least one interfering RNA molecule that binds to an area of transcript containing a region that corresponds to at least one sequence having SEQ ID NO: 1, the interfering RNA molecule regulating the expression of the transcript through post-transcriptional silencing. In another aspect, a method for regulating the expression of a transcript comprises at least one of the provided sequences having SEQ ID NO: 1 being used to design an interfering RNA molecule that contains a region that corresponds to the reverse complement of one or more sequences having SEQ ID NO: 1, the interfering molecule regulating, through post-transcriptional silencing, transcripts that contain the sequence having SEQ ID NO: 1.

1 Claim, 23 Drawing Sheets

NOTE: THE PROBABILTY DENSITY AND CUMULATIVE FUNCTIONS FOR THE LENGTHS THE ENTIRE COLLECTION OF BLOCKS, $P_{init}$, THAT THE PATTERN DISCOVERY STEP IDENTIFIED IN THE HUMAN INTERGENIC AND INTRONIC REGIONS.

FIG. 3

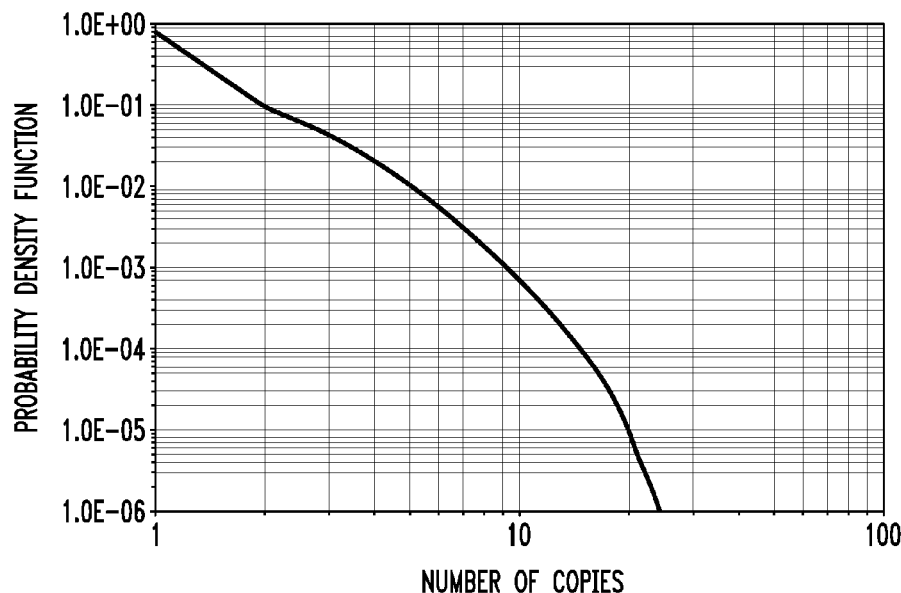

NOTE: THE PROBABILITY DENSITY FUNCTION FOR THE NUMBER OF INTERGENIC/INTRONIC COPIES OF FIXED-SIZE 16-mers THAT ARE DISCOVERED IN A RANDOMLY-SHUFFLED VERSION OF THE INPUT SET.

FIG. 4

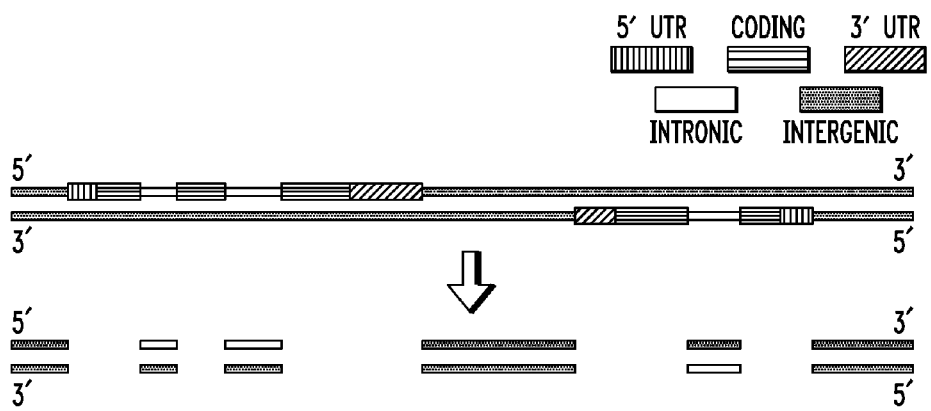

NOTE: PREPROCESSING OF THE INTERGENIC/INTRONIC SEQUENCES PRIOR TO CARRYING OUT PATTERN DISCOVERY. ALL SEQUENCE SEGMENTS THAT CORRESPOND TO THE UNTRANSLATED AND CODING REGIONS OF KNOWN GENES OR THAT ARE THE REVERSE COMPLEMENT OF THE UNTRANSLATED AND CODING REGIONS OF KNOWN GENES ARE REMOVED. TOP: GENOMIC INPUT BEFORE THE PREPROCESSING. BOTTOM: INPUT ON WHICH PATTERN DISCOVERY WILL BE RUN.

FIG. 5

| | | |
|---|---|---|
| 10 | TCCCATACCACGGGGATT | (SEQ ID NO: 747,328) |
| 9 | TCCCATACCACGGGGATTA | (SEQ ID NO: 747,329) |
| 9 | CTCCCATACCACGGGGATT | (SEQ ID NO: 747,330) |
| 8 | CTCCCATACCACGGGGATTA | (SEQ ID NO: 747,331) |
| 8 | TCCCATACCACGGGGATTAC | (SEQ ID NO: 747,332) |
| 7 | GCCTCCCATACCACGGGGATT | (SEQ ID NO: 747,333) |
| 7 | TCCCATACCACGGGGATTACA | (SEQ ID NO: 747,334) |
| 5 | GCCTCCCATACCACGGGGATTA | (SEQ ID NO: 747,335) |
| 4 | GCCTCCCATACCACGGGGATTACA | (SEQ ID NO: 747,336) |
| 4 | GGCCTCCCATACCACGGGGATTA | (SEQ ID NO: 747,337) |

NOTE: AN EXAMPLE OF VARIATIONS ON THE SAME THEME. SEVERAL VARIATIONS OF THE SAME CORE PATTERN (SHOWN IN BOX) ARE LISTED IN ORDER OF INCREASING SPECIFICITY AND THUS IN ORDER OF DECREASING NUMBER OF APPEARANCES. THE NUMBER OF APPEARANCES PRECEDES EACH PATTERN.

FIG. 6

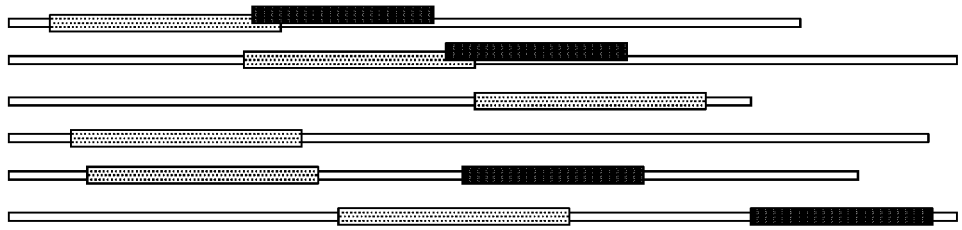

NOTE: DETERMINING LOGICALLY DISTINCT PATTERNS. THE LIGHTER RECTANGLE REPRESENTS ONE BLOCK WITH SIX INSTANCES WHEREAS THE DARKER RECTANGLE REPRESENTS ANOTHER BLOCK WITH FOUR INSTANCES.

NOTE: THE PROBABILITY DENSITY FUNCTION FOR THE LENGTHS OF THE PYKNONS - IT IS SHOWN SEPARATELY FOR EACH OF $P_{5'UTR}$ (LINE MARKED WITH △ ), $P_{CODING}$ (LINE MARKED WITH (○) AND $P_{3'UTR}$ (LINE MARKED WITH □).

NOTE: NUMBER OF BLOCKS THAT ARE SHARED BY THE THREE SETS WHOSE UNION MAKES UP THE PYKNON COLLECTION.

NOTE: THE CUMULATIVE FUNCTION FOR THE NUMBER OF INTERGENIC AND INTRONIC COPIES OF THE PYKNONS – IT IS SHOWN SEPARATELY FOR EACH OF THE SET $P_{5'UTR}$ (DASHED LINE), $P_{CODING}$ (DASHED-DOT LINE) AND $P_{3'UTR}$ (SOLID LINE).

NOTE: CUMULATIVE FUNCTION THAT SHOWS WHAT PERCENTAGE OF THE AFFECTED 30,675 TRANSCRIPTS CONTAINS N OR MORE PYKNON INSTANCES IN THEM.

FIG. 11A

Note: Combinatorial arrangements of pyknons in 3'UTRs are shown for the apoptosis inhibitor birc4 (shown above the horizontal line) and nine more genes. The sequences below the horizontal line contain some of birc4's pyknons but in different arrangements: they also contain instances of other pyknons that are not present in birc4's 3'UTR. Each of the ten shown 3'UTRs is a mosaic pyknons. The pyknons in this Figure, have by definition 40 or more instances in the genome's intergenic/intronic regions and *additional* copies in the untranslated and coding regions of these and other genes. The string -(xx)- indicates that xx nucleotides separate the pyknons that surround it. To appreciate the importance of this picture it suffices to keep track of the number of copies and the relative position of the four pyknons TGCACTCCAGCCTGGG (SEQ ID NO: 747,338), TAATCCAGCACTTTGGGA (SEQ ID NO: 747,339), GGCTGAGGCAGGAGAAT (SEQ ID NO: 747,340) and GAGGTTGCAGTGAGCC (SEQ ID NO: 747,341) in these ten 3'UTRs. Of the nine transcripts shown below the horizontal line: ENST00000338356 encodes a carboxypeptidase M precursor; ENST00000313852 encodes a protein with a bipartite nuclear localization signal; ENST00000361561 encodes a protein with an instance of the RUN domain; ENST00000305513 encodes a protein with a zinc-finger domain; ENST00000259393 encodes a high-affinity copper-uptake protein; ENST00000356694 encodes a protein with an ankyrin repeat; ENST00000295102 encodes a protein phosphatase 2A regulatory subunit that contains a WD-40 repeat; and, ENST00000360166 and ENST00000362058 encode proteins with unknown function.

(SEQ ID NO: 747,342).

>3'UTR OF ENST00000245836[ENSG00000101966_CHR=X_STRAND=FORWARD
-(162)-TTTCTTGATTTTCAG-(104)-ATACTGATTAATTC-(208)-ATTTCTTTTAAAGTT-(91)-ACTGACATGGAAAGAT-(243)-TGTATTACTTTTGTAA-(5)-AT
TTTAGAAAGTATT-(146)-TGGATGAAAAATATTT-(591)-CTCACACAACAAACCTAT-(139)-ATTCATTTAAACATT-(27)-CTTTTTGAGATGGAGTCTT-(8)-CCCA
GGCAGAGTGCA-(8)-ATCTCTGCTCACTGCA-(6)-GCCTTCTGGGTTCAAG-(2)-ATTCTCGTGCCTCAGC-(6)-AGTAGTGGAATTACAG-(6)-GCCACCATGCC
CGACTA-(39)-TTGGCCAGGCTGGTAT-(2)-AACTCCTGACCCTCAG-(19)-TCCCAAAGTGCCAGGCTTGAGCACCTA-(724)-TTATTTTACATTTA
G-(333)-AAATTTGTATTTTGAA-(186)-CAGTGCCGGGGCGTGGTGG-(7)-CTGTAGTCCCAGCACTT-(5)-GGCTGAGGCAGGAGAATGGTGTGAACCCGGGAGG-(2)-G
A-(13)-TCTCTACTAAAAAACA-(5)-TTAGCGCGGGCAGCCTGG-(4)-AGAGCAAGACTCTGTC-(101)-TCTGTGAAAGGAAAT-(69)-ACTCCCATCCTAATAC-(137)-CGGT
AGCTTGCAGTGAGCC-(13)-TGCACTCCAGCCACTTTGGGA-(14)-GATCACCTGAGGTCGGGAGG-(3)-AGACCAGCCTGAGGTGGAGCG-(13)-TAAGCTGGGCGTGGTG-(8)-CTGTA
ATCCCAGCTACT-(5)-GGCTGAGGCAGGAGAAT-(2)-CTTGAACCCAGGAGG-(1)-GAGGTTGTGTGAGCA-(13)-TGCACTCCAGCCTGGGCAACAAGAGCA
AAACT-(58)-TTAGCCAGGCGTGGTG-(16)-GCAGCTACTCTGGAGG-(1)-AGAGGCAGGAGGATCACTTGAGCCATGAATT-(1)-GAGGCAGCAGTGAGCT-(13
)-TGTACTCCAGTCTGGG-(2)-ACAGAGTGAGACCCCA-(50)-TTGAAAAGATTATTCT-(166)-TCATTTTACAGGTGAG-(258)-CCAGCCTGGACAAAAG-(3)-AAACCCTGTC
TTGTTAAGCAACA-(3)-TAACAACTATTTACAT-(37)-AGCAATTATTTTTAAA-(12)-ATTGTATTAGGTATTA-(33)-TGGAAAAGTGCTCAGTGAGCT-(13)-TGCATTCCAGCC
TCTACAAAA-(10)-TTAGCTGGGCATGGTG-(9)-TGTAGTCCCAGCTACT-(15)-GGAGGATCGCTTGAGT-(10)-GAGGCTGCATTGAGCT-(13)-TGCATTCCAGCC
TGGG-(10)-AGACCTTGTCTCAGAA-(31)-GTGCCCAGTTAATTTTTTTTTGTATTCTTAGTAGAGA-(15)-TTGGCCAGGCTAGTCT-(2)-AATTTCTGACCTCAGGCTCAT-(20)-C
AGCTGGACAGG-(11)-GTGCCGATTACAGGCGTGAGCACGGGCCACCA-(47)-TTGACCAGGCTGGTCT-(2)-AACTCCTGAGGCAGG-(3)-CTCACCTGAGGTCAGGAGTT-(2)-AGACCAGCCTGGGATTACA
GTGCTGGGATTACAGGCGTGAGCACGGGCCACCA-(125)-GGCACGGTGGCTCACGCCT-(16)-CCGAGGTCCCAGATGGTG-(8)-CTGTAGTCCCAGCATGGTG-(8)-CTGTAGTCCCAGCATGGTG-(8)-GAGGT
CCTGCTGTACAAAAA-(7)-ATAGCTGGGCATGGTG-(8)-CTGTAGTCCCAGCTACT-(6)-ACTGAGGCAGGAGAAT-(2)-CTTGAACCTGGGAGGC-(1)-GAGGT
GGAGAGCC-(13)-CGCACTCCAGCCTAGG-(1)-GATAGAGTGAGACTCC-(327)-ATGTTTTGAGACAGAG-(56)-GAAAACTAAGAAAATT-(41)-TTATTTTCT
GTGAAT-(10)-CAATAAAATACTATTC-(10)

FIG. 11B (SEQ ID NO: 747,343):
>3'UTR OF ENST00000305513|ENSG00000186532_CHR=17_STRAND=REVERSE
-(66)-GCCAGGTATGGTGGCT-(8)-TAATCCCAGCACTTTGGGA-(15)-ATCACCTGATGTCAGGAGTT-(2)-AGACCAGCCTGGCCAA-(36)-ACTAGCCAGGCGTG-(8)-CTGTAATCCCAGCTACT-(5)-GGCTGAGGCAGGAGAAT-(2)-CTTGAACCCAGGAGGC-(1)-GAGGTTGCAGTGAGCC-(10)-CACTGCACTCCAGCC-(2)-GTGACAGTGAGACT-(32)-CGGTGGCTCAAGCCTGTAATCCCAGCACTTTGGGA-(14)-GATCACGAGGTCAGGAG-(4)-AGACCATCCTGGCTAACA-(37)-TAGTCGGGCGTGGTGG-(6)-CCTGTATTCACAGCTA-(5)-GAGGTTGAGGCAGGAG-(4)-GGGTGAACCCGGGAGG-(2)-GAGCTTGCAGTGAGCC-(13)-TGCAC-TCCAGCCTGGG-(1)-GACAGAGCCAGACTCC-(140)-AGGCTCACACCTGTAATCC-(11)-GACGCTGAGGTGGGAGGATCACTTGAGCCCAGGAGTT-(1)-TGG-GCAATATAGTGAGA-(8)-CTACAAAAAAGTTTT-(1)-AGCATGGTGGCACATG-(1)-CTGTAGTCCCACCTACT-(14)-AGGGTCACCTGAGCCT-(8)-GAGGCTG-CAGTGAGCC-(13)-TGCACTCCAGCCTGGG-(4)-AGAGTAAGACCCTGTC-(547)-TTTTATTGAGCAGTTT-(121)-

(SEQ ID NO: 747,344):
>3'UTR OF ENST00000338356|ENSG00000135678_CHR=12_STRAND=REVERSE
-(312)-AAAGAAGATCATTTTG-(83)-AGCAGTGGCTCACACCT-(2)-TAATCCCAGCACTTTGGGA-(5)-AGGTGGGCGGATCACCC-(16)-AAACCAGCCTGACCA-ACATGGTGAAACCCTGTCTCTACTAAAT-(1)-TTAGCGGGGTGGGTG-(4)-GCACCTGTAATCGCAG-(8)-GAGGCTGAGACAGGAG-(5)-CTTGAACCCTAGAG-GC-(1)-GAGTTGCAGTGAGCC-(9)-CCATTGTACTCCAGCT-(10)-AGTAAGACTCTGTCTC-(525)-TGGGAGTCATCCTTGA-(56)-GGCCAGGCATGGTGGC-(9)-TAATCCCAGCATTTGGGA-(21)-TGAGGTCAGGAGCTCAAGACCAGCCTGGCCAA-(40)-TAGTCGGGGCGTGGTGG-(7)-CTGTAATCCCAGCTACT-(5)-GGCT-GAGGCAGGAGAAT-(2)-CTTGAACCTGAGGTCAGGAGC-(1)-GAGGTTGCAGTGAGCC-(13)-TGTACTCCAGCCTGGG-(6)-AGTGAGACTCTGTCTT-(17)-CTGATAAA-TATTGATG-(279)-CAGCTCCACTAGGAAG-(18)-CCATTCAATTCAATT-(132)-GAGCTCTTTGAGGCCA-(46)-CCTAGCACATAGTAGG-(3)-TGAATGAATGAA-TGAA-(60)-TCATTTTATGAAGCTA-(171)-TTTTATCAGAAAAAAAA-(305)-ACTTAATCCCAGCTGT-(132)-ACAAAGGAATGAAGAG-(7)-AGCATTTAGGCCATT-(646)-AAATGGTATTTAGAAA-(14)-CGGTGGCTCATGCCTGTAATCCCAGCTACT-(4)-AGGCTGAGGCAGGAGAAA-(3)-CCTGAACCCAGAAGGC-(1)-GAGGTTGCAGTGAGCC-(15)-GG-0)-TTAGCCCGGGCGTGG-(7)-CTGTAACCCCAGCT-(4)-AGGCTGAGGCAGGAGAAA-(3)-CCTGAACCCAGAAGGC-(1)-GAGGTTGCAGTGAGCC-(15)-GG-CACTGCACTCCAGCCG-(15)-CCTCTGTCTCAAAAAAA-(65)-TTTCTTTATCTGTAAA-(419)-GTTTAGAAAGTAAAAA-(458)-CCCAGGTTGGAGTGCA-(13)-GG-CTCACTGCAACCTC-(1)-GCCTCCCGGGTTCAAG-(5)-CTCCTGTCTCAGCCTC-(2)-GAGTACCTGGGACTAC-(16)-GCCCGGCTAATTTTTGTATTTGTAGTAG-AGA-(13)-TGTTAGCCAGGATGGTCT-(4)-CTCCTGACCTCATGATC-(20)-TCCCAAAGTGCTGGGATTACAGGCGTGAGCCCCCG-(151)-

(SEQ ID NO: 747,345):
>3'UTR OF ENST00000360166|ENSG00000197291_CHR=17_STRAND=REVERSE
-(62)-CCTGTTGTGGGAGGG-(794)-CGGTGGCTCATGCCTG-(1)-CATCCCAGCACTTTGGGA-(17)-AACCTGAGGTCAGGAGTT-(13)-AACAACATGGTGAAA-C-(42)-TGCCTGCCTGTAATCC-(10)-GAGGCTGAGGCAGGAAAGGC-(1)-GAGGTTGCAGTGTGCC-(10)-CACTGAACTCCAGCCT-(3)-CAACAAGAGTGAAACT-(111)-TATTGAACACTTACTA-(148)-GCAGAGCCAGGATTT-(244)-TGTTTTTAAAAGAA-(386)-TTTACAGACAAGGAAA-(23)-GGCCAGGCATGGTGGC-(9)-TAATCCCAGCAGTTTGGGAGGGCTGAGGTGGGAGGA-(6)-CTTGAGCCCAGAAGTTGAGGCTGCAGTGAGCC-(11)-CCATCTCTACAAAAA-(1)-TTAT-CTGGGCCTGGTG-(8)-CTGTAGTCCCAGCTACT-(2)-AGAGGCTGAGGCAGGAGGTGGGA-(6)-CTTGAGCCCAGAAGTTGAGGCTGCAGTGAGCC-(13)-TGTACTCCAGCC-TGGG-(3)-CAAAGCAAAACCCTGT-(27)-CGGTGGCTCACACCTGTAATCCCAACACTTTGGGA-(15)-ATCACCTGAGGTCAGGAGTT-(2)-AGACCAGCCTGGC-CAA-(14)-CCTCTACTGAAAATACAAA-(9)-GCATTGTGGCACATG-(12)-ATCACCTGAGGTCAGGAGTT-(12)-AGACCAGCCTGGCCAA-(36)-TTAGCTGGGC-GTGGTG-(8)-CTGTAGTCCCAGCTACT-(5)-GGCTGAGGCAGGAGAAT-(2)-CTTGAACCTGGCAGT-(1)-GAGGTTGCAGTAAGCC-(13)-TGCACTCCAGCCTG-GG-(6)-

FIG. 11C (SEQ ID NO. 747,346):

>3'UTR OF ENST00000313852|ENSG00000180488_CHR=1_STRAND=FORWARD
-(140)-ACTGTACTGTATTTAT-(86)-AGACTAGCCTGGACAA-(16)-TCTCTACAAAAACATAAAATAATTAGCTGG-(45)-AAAAATAGGCTGGGTGTGGTTCATGCC
-(1)-TTGAGGCCAGGAG-(4)-AGACTAGCCTGGACAA-(16)-TCTCTACAAAAACATAAAATAATTAGCTGG-(45)-AAAAATAGGCTGGGTGTGGTTCATGCC
TGTAATCCAGCACTTTGGGA-(13)-GGATCACCTGAGGTCAGGT-(16)-CCCAATATGGTGAAAC-(26)-TAGCCAGGTGTGGTGG-(7)-CTGTAGTCCAGCTAC
T-(3)-GAGGCTGACAGGAG-(5)-CTTGAACCCAGGAAGT-(1)-GAGGCTGCAGTGAGCC-(13)-TGCACTCCAGCCTGGG-(6)-AGTGAGACTGTCTC-(36)-G
TGTGGTGGCATGTGT-(1)-TGTGGTCCCAGCTACT-(31)-CCAGAAGGTCAAGCT-(4)-TGAGCTGTGATTGCAT-(3)-TGCACTCCAGCCTGGG-(44)-AGCAAGAC
CCTATCTC-(51)-AATTTACAATTTACAA-(60)-CTGAAGAACTTCTTT-(418)-ATTTTGTTTCTAAATA-(140)-AGAGATGGGGTCTCGCT-(6)-CCCAGGCTGGAG
TGCA-(15)-TAGCTCACTGCAGTCT-(45)-AAATGCATTTTAAAA-(27)-TTCTGATTAATAAAT-(55)-TGTATGTGCCACATTT-(276)-CACACACATGTGTG-(5
9)-CAGTGGCTCAGCGCCTGTAATCCCAGCACTTTGGGA-(17)-AACCTGAGGTCAGGAGTT-(2)-AGACCAGCCTGACCAA-(36)-TTAGCCAGGCATGGTG-(8)-C
TGTAATCCCAGCACT-(5)-GGCTGAGGCAGGAGAAT-(2)-CTGAACCCGGGAGGC-(1)-GAGGTTGCAGTTAGCC-(13)-TGCACTCCAGCCTGGGCAACAAG
AGTAAAACT-(7)-

(SEQ ID NO. 747,347):

>3'UTR OF ENST00000259393|ENSG00000136868_CHR=9_STRAND=FORWARD
-(128)-CACACACACACCCCTG-(50)-AATTGTTTTTCTAAT-(135)-CTTTTGAATTTTTAA-(153)-CAGTGCCCATGCCTGTAATCCCAGCACTTTGGGG-(16)-
ATCACCTGAGGACAGGAGAGTT-(2)-AGACCAGTCTGGCAA-(37)-TAGCCGGGCATGGTGG-(7)-CTGTAATCCCAGCTACT-(5)-GGCTGAGGCAGGAGAAT-(2)-
CTTGAACCCTAGGAGGC-(1)-GAGGTTGCAGTGAGCC-(13)-TGCACTCCAGCCTGGG-(1)-GACAAGAGTGAAACTC-(340)-TTTGAATTAATTTTC-(23)-GCCTC
TAAACTGTGA-(17)-GCATCAGAATCACCTG-(1)-AGGGCTGTGTTAAACA-(227)-ACATTTATTGAGCTCC-(502)-AGGGCAGGAGAAACAA-(424)-CAATGGC
TCATGCTGTAATCCCAACACTTTGGGAGGCCAAGGTGGGAGGA-(21)-AGACCAGCCTGAGCACAA-(3)-AGTGAGATCCTATCTC-(16)-TTAGCCAGGCATGGT
G-(7)-CCTATAGTCCTGGCTA-(8)-GCTGAGGCAGGAGGAT-(20)-AGGCTGGGCAGGAGCC-(7)-GCCACTCCAGCCTGGG-(10)-AGCAAGAGCCTGTCTC-(880)-C
TCTGGGCTGGGCACAG-(7)-CACACTTGGGAGGCC-(14)-ATCACCTGAGGTCAGGAGTT-(12)-AGACCAGCCTGGCCAA-(36)-TTAGCTGGGCGTGGTG-(8)-C
TGTAATCCCAGCTACT-(5)-GGCTGAGGCAGGAGAAT-(2)-CTTGAACCCAGGAGGC-(1)-GAGGTTGCAGTGAGCC-(1)-GAGGTTGCAGTGAGCC-(13)-TGCACTCCAGCCTGGG-(1)-GACAA
GAGCAAAACTC-(183)-

(SEQ ID NO. 747,348):

>3'UTR OF ENST00000362058|ENSG00000186543_CHR=1_STRAND=REVERSE
-(776)-TGTCACCCAGCTGGAG-(90)-TGGTTGGAGCAGGAGG-(330)-CAGTGGCTCACGCCTA-(17)-GAAGCCGAGGCGGGTGGATCACC-(16)-AGACCATCCT
GGCTAACA-(9)-CCTATCTCTACAAAAA-(1)-TTAGCTGGGTGTGGTG-(8)-CTGTAGTCCCAGCTACT-(5)-GGCTGAGGCAGGAGAAT-(6)-AACCTCTGCCTCCG
GG-(14)-CCTGCCTCAGCGTCC-(1)-AGTAGCAGGGACTACA-(2)-CGTGCACCACCACATGCCCG-(10)-GTATTTTAGTAGAGA-(15)-TTGGCCAGGCTGGTCT-(
2)-AACTCTTGACCTCAAG-(10)-GCCAAAGTGCTGGGATTATAGGCGTGAGCCACCG-(116)-CTGCCAGGACTGGTT-(688)-TGGGGACTTGGGGGAA-(142
)-CCTCTCTGGGCTGCAG-(699)-AGTTTCACTCTTGTTGCCCAGGCTGGAGTGCA-(14)-GCTCAACCTCCCAGGTTCAAG-(2)-ATTCTCCTGC
CTCAGCC-(5)-AGTAGCTGGGATTACAG-(12)-ATGCCTGGCTAATTTTGTATTTTAGTAGAGA-(22)-AGCTGGTCTCGAACTC-(13)-ATCTGCCCACTTCGGCC
TCCAAAGTGCTGGGATTA-(1)-AGGCATGAGCCACCGC-(21)-GAGACAGAGTCTCACT-(7)-CCCAGGTTGGAGTGCA-(8)-ATCTGAGCTCACTGCA-(6)-GCC
TCTGGGTTCAAG-(2)-ATTCTCCTGCCTCAGCC-(5)-AGTAGCTAGGACTACA-(9)-CACCATGCCCAGCACCTG-(90)-GGAAAGGGGTCAGGGC-(23)-GGAAACTGGA
GCCCAG-(51)-CTCTGCCTCTGGGATT-(213)-GTGGGCAGCCCAGGAG-(107)-CATCTGTGAAATGGGA-(289)-TGCCTGGGTTTGAATC-(37)-TCTGTGCCTTC
ATTTC-(318)-GCTGGGATTCCAGGCA-(61)-TAATCCCAGCCACTTTGGGA-(14)-GATCACGAGGTCAGGAG-(4)-AGACCATCCAGCTAACA-(1)-AGTGAAACC
CTATCTC-(18)-TTAGCTGGGCATGGTGG-(9)-TGTAGTCCCAGATACT-(8)-TAAGGCAGGAGAATGCTTCAACCTGGGAGGC-(1)-GAGGTTGCAGTGAGCC-(13
)-TGCACTCCAGCCTGGG-(21)-

FIG. 11D (SEQ ID NO: 747,349):
>3'UTR OF ENST00000361561|ENSG00000198863_CHR=17_STRAND=FORWARD
-(225)-CGGTGAGTCCAGCTACT-(6)-GGCTGAGGCAGGAGAATGGCGTGAACCAGGAGG-(2)-GAGCTTGCAGTGAGCC-(13)-TGCACTCCAGCCTGGG-(1)-GA
CAGAGTGAGACTCC-(86)-CAGTGGCTCACGCCTG-(9)-CACATTGGAGGCTGAGG-(7)-ATCACCTGAGGTCAGGAGTT-(2)-AGACCAGCCTGGCCAA-(60)-C
TGTAATCCCAGCTACT-(3)-CTTGAGCCCGAGAA-(3)-CTTGAGCCCAAGATCATGCCA-(1)-TGCACTCCAGCCTGGGCAACA
CAGGGAGACTC-(84)-TTTGAGAGGCTAGGC-(160)-TTTTTCTTGTAGAGGT-(492)-CAAAAATGGGCAAAT-(344)-

(SEQ ID NO: 747,350):
>3'UTR OF ENST00000356694|ENSG00000197256_CHR=19_STRAND=REVERSE
-(41)-TTTTGTTTTGAGGC-(14)-TCGCCCAGGGTGGAGT-(16)-GGCTCATTGCAACCTC-(1)-GCCTCCCGGCTTCAAG-(5)-CTGCTGCCTCAGCCTC-(2)-GAG
TAGCTGGGGATAACAGGTGTGTGGCGCATGCCT-(7)-CAGCTATTCTGGAGGT-(15)-CTTGAACCCAGGAGGT-(1)-GAGGTTGCAGTGAGCC-(18)-CAACAA
GCAGCAAAACT-(82)-AAGAGAATGACATTTGA-(8)-TGCAAAGGCCCTGAGG-(59)-TAATCCCAGCACTTTGGGA-(15)-GCTGAGGCCTGAGGTCAGGAGTT-(2)-AGA
CCAGCCTGGCAA-(36)-TTAGCTGGGTGTGTG-(8)-CTGTAATCCCAGATACT-(6)-GGAGGTTGCAGTGAGGC-(6)-TGCAGTGA
GCTGAGAT-(8)-TGCACTCCAGCCTGGC-(6)-TAGCTGGGCCTGGTGG-(8)-TATAGTCCCAGCTACT-(3)-GAGGCTAAGGCAGGAG-(29)-CTGTGAGCTATGA
TTG-(6)-TATACTCCAGCCTGGC-(6)-GCAAGACCCTGTCTT-(4)-AAAAAAAATCTAGGC-(2)-GGCACGGTGGCTCACGCCT-(1)-TAATCTCAACACTTTG-(18
)-ATCACCTGAGGTCAGGAGTT-(2)-AGACCAGACTGAGCAA-(1)-TCTCTACTAAAAACGCAA-(15)-TTAGCCGGGCGTGTGG-(7)-CTGTAATCCCAGCTAC
T-(5)-GGCTGAGGCAGGAGAAT-(2)-CTTGAACCCAGGAGGC-(6)-TGCACTCCAGCCTGGGCAACAAGAGTGAAACT-(7)-

(SEQ ID NO: 747,351):
>3'UTR OF ENST00000295102|ENSG00000143940_CHR=2_STRAND=FORWARD
-(112)-TCCTCTGTCTCTGCCT-(363)-TTGAATTTTGTAAAAT-(182)-CAGTGGCTCACACCTGTAATCCCAGCCCTTTGGGA-(2)-CTGAGGCAGGTGGATT-(1)-C
TTGAGCCCAGGAGTT-(16)-CTCATCTCTACAAAAA-(11)-GTGGTGGGCGTGTACCTCTAGTCCCAGCTACCC-(43)-CTAGGCTGCAGTGAGC-(14)-TGCACTCC
AGCCTGGGT-(2)-ACAGTGGCCTGTC-(175)-AAAAAAAATTTTTCTG-(54)-ACTGAGCACTTAAAAT-(148)-AAAATGTTACTGAAAT-(43)-ATCATGTTATTT
TCT-(116)-TTGGAAAATATTTTAA-(284)-TTTTGTTGAAAGCAAA-(1695)-ATATTCACTTTTTAAA-(826)-ATACATATTTACATAA-(63)-ATAGAAACTTTTAAAA-
(10)-GGGCATGGTGGCTCAC-(5)-TAATCCCAGCCGTGGT-(6)-GAGGTGGGCGGATCTCCTGAGGTCAGGAGTTC-(1)-AGACCAGCCTGGCCAA-(1)-ATGGTG
AAACCCGTCTT-(17)-TAGCCAGGCCTGG-(1)-GACAGAGTGAGACTCC-(413)-TGAGAATATTTTAAAT-(80)-ATTTTATTTTCAAGAT-(130)-TCATTCCAATTTAGT-(
AGCC-(13)-TGCACTCCAGCCTGGG-(1)-TAATCCCAGCACGCGG-(13)-TAATCCCAGCACTTTGGGA-(14)-GATCACGAGGTCAGGAG-(4)-AGACCATCCTGGCTAACA-(34)-ATTAGCCAGGCCT
258)-CAAAGGCCGGCGCGG-(13)-TAATCCCAGCACTCCAGCTACT-(3)-GAGGCTGAGGCAGGAGAACCCGGCAGGAGGAACGGCGTGAACCCAGG-(2)-GAGCTTGCAGTGAGCC-(13)-TGCACTCCAGCCTAGG
GGT-(9)-CTGTAGTCCCAGACTCC-(5)
-(1)-GGCAGAGCCAGACTCC-(5)

| FIG. 11A |
|---|
| FIG. 11B |
| FIG. 11C |
| FIG. 11D |

Note: 5'UTRs for ENSG00000196809 a human gene of unknown function and eight more genes. The shown 5'UTRs are mosaics composed of pyknons. The shown pyknons have 40 or more copies in the genome's intergenic and intronic regions. The string (xx) indicates the number of nucleotides, xx, that separate the surrounding pyknons. To appreciate the importance of the result in this Figure, it suffices to keep track of the number of copies and relative arrangement in each of the shown 9 genes of the four pyknons TCCCAAAGTGCTGGGATTA (SEQ ID NO: 747,352), CCCAGGCTGGAGTGCA (SEQ ID NO: 747,353), AGTAGCTGGGATTACAG (SEQ ID NO: 747,354) and AACTCCTGACCTCAGGTGAT (SEQ ID NO: 747,355). Below the solid line are the 5'UTRs for eight other transcripts: ENST00000314752, a monoamine-sulfating phenol sulfotransferase which is involved in catecholamine/lipid/steroid metabolism; ENST00000287474, a gene whose product has dopamine beta-monooxygenase activity and is involved in catecholamine metabolism; ENST00000344420, that encodes a centromere protein involved in nucleosome assembly, chromosome organization and biogenesis; ENST00000355921 a zinc finger protein involved in transcription regulation; ENST00000358920, that encodes a gene of unknown function; ENST00000357256, a surfeit locus protein; ENST00000355587, a Huntingtin interacting protein; and, ENST00000326880, that encodes a peptide-chain release factor.

(SEQ ID NO: 747,356)

>5'UTR OF ENST00000358509|ENSG00000196809_CHR=22_STRAND=FORWARD_UPSTREAM_UTR
-(704)-TTCTTCATTCATTCA-(53)-GACAGTCTCGCTCTGT-(2)-CCCAGGCTGGAGTGCA-(8)-ATCTCAGCTCACTGCA-(6)-GCCTTCCAGGTTCAAG-(2)-AGTC
TCCTGCCCTCAGCCTC-(3)-AGTAGCTGGGATTACAG-(9)-ACCACGCCTGGCTAATT-(4)-CATTTTAGTAGAGACG-(3)-CTTCACCATGTTGGCCA-(11)-AACTC
CTGACCTCAGGTAAT-(11)-TCCCAAAGTGCTGAGATTA-(5)-GTGAGCTACCGTGCCC-(216)-GGTGGTCAGGGAAGGC-(64)-AGGGAGGAGGAACAGC-(192)-
TTCATTCAACAAATAT-(931)-TGCCCAGGCTGGAGTT-(10)-AGCTCACTGCAACCTCCCAGATTCAAGATTCT-(17)-AATAGCTGGGACTACA-(5)
-ATGTCACCATGCCCAG-(42)-TTGGCCAGGCTGGAGTGCA-(13)-GGCTCATTGCAACCTC-(1)-AATCTACCTGCCTTGG-(2)-TCCAAAGTGCTAGGATTACAGGTGT
GAGCCACCG-(87)-CCCAGGCTGGAGTGCA-(13)-GGCTCATTGCAACCTC-(1)-ACCTCCCGGGTTCAAG-(13)-TCAGCTTCCTGAGTAGCT-(5)-TACAGGCACT
TGCCAC-(32)-GACAGGGTTTTGCCAT-(1)-TTGGCCAGGCTGGCCAT-(2)-AACTCCTGACCTCAGGTGAT-(15)-TCCCAAAGTGCTGGCATTA-(2)-GGCTTGAGC
CACCACG-(351)-GGAGTCTCGCTCTGTC-(6)-GCTGGAGTGCAGTGAC-(1)-TGATCTCGGCTCACTGCAG-(1)-CTCCGCCTTCTGGGTTCA-(4)-ATTCTCCTGC
CCTCCC-(3)-AGTAGCTGGGACTACAG-(7)-COACCTCGGCTGGCTA-(36)-TGTTAGCCAGGATGGTCT-(4)-CTCGTGACCTCGTGATC-(2)-CCAGCCTCGG
CCTCCC-(20)-TGAGATGGAGTTCGC-(9)-TCAGGCTGGAGTGCAATG-(5)-ATCTCAGCTCACTGCA-(6)-GCCTCCCAGGTTCAAG-(2)-ATTCTCCCACCTCAG
C-(6)-AGTAGCTGGGATTACAG-(45)-GGGGTTTCACTATGTTGGCCAGGCTGGTCTTGAACCTCTGACCTCAGGTGAT-(15)-TCCCAAAGTGCTGGGATTA-(14
5)-TGGAGGTAGGGCCTGG-(49)-TGAATGAAAGAAATGAA-(4)-TTTGGGAGGCCAAGGTGGGT-(2)-ATCACCTGAGGTCAGGAGTT-(2)-AGACCAGCCTGGCC
AA-(15)-CCTCTACTAAAATACAAAAAATTAGCTGGGCGT-(9)-TGCCTGTAATCACAGC-(7)-GAGGCTGAGGCAGGAGAAT-(19)-GAGGTTGCAGTGAGCC-(
7)-TGCCATTGCACTCCAG-(4)-GGCAACAGAGCGAGACT-(584)-

FIG. 12B (SEQ ID NO: 747,357):

>5'UTR OF ENST00000314752|ENSG00000132207_CHR=16_STRAND=FORWARD_UPSTREAM_UTR
-(5)-GAGTCTTGCTCTGTTG-(2)-GAGGCTGGAGTGGATCTCAGCTCACTGGA-(6)-GCCTCCTGGGTTCAAG-(11)-TCTCAACCTCCCAAGT-(1)-TGCCAC
CACACCTGCC-(11)-TTTTAGTGGGATGG-(11)-TTGGGCAGGCGTGCT-(2)-AACTCCTGACCTCAAG-(19)-TCCCAGGCTGTGGGATTA-(6)-TGAGCCAC
CATGCCTG-(8)-CCTGTCTCTAAAACAA-(190)-CAGAAATTTCTTTT-(23)-GAGACAGAGTCTTACT-(3)-TCGCTCAGGCTGGAGT-(11)-ATCTCAGCTCACTG
CAACCTCGCCTCCCTGGT-(11)-CTCCTTCCTCAGCCTC-(3)-AGTAGCTGGGATTACAC-(7)-CCACCGCGCCTGGCTA-(38)-TTGGCCAGGCTGGTCT-(2)-AACT
CCTGACCTCAGGTGAT-(12)-AGCCTGCCCAAATGCT-(7)-CAGGCATGAGCCACCG-(239)-CTCAGTTTCTTCATTT-(77)-GGGGTTGCTGCCAGCTG-(262)-

(SEQ ID NO: 747,358):

>5'UTR OF ENST00000287474|ENSG00000156869_CHR=1_STRAND=REVERSE_UPSTREAM_UTR
-(4)-TGCTGGGATTACAGGCGC-(5)-ACCACGCCCGGCTAAT-(23)-GGGTTTCACTGTGTTG-(3)-AGGATGGTCTCTATCTC-(8)-GTGATATGCCCGCCTC-(4)-TC
CCAAAGTGCTGGGATTACAGGCTTGAGCCACCG-(5)-GGCCTATTTATTTATT-(6)-GAGACGGAGTGTTGCT-(7)-CCCAGGCTGGAGTGCA-(13)-GGCTCACT
GCAACCTC-(1)-GCCTCCCGGGTTCAAG-(2)-ATTCTCCTGCCTCAGCCTC-(3)-AGTAGCTGGGATTACAG-(12)-ACACCCGGCTAATTTGTATTTTAGTAGAA
A-(2)-GGGTTTCTCCATGTTG-(6)-CTGGTTTCGAACTCCC-(8)-GTCATCTGCCTGCCTC-(4)-TCCCAAAGTGCTGGGATTACAGGCGTGAGCCACCG-(12)-TCT
GTATTTTAAAAA-(21)-TAAATGATTTGCCCAA-(72)-

(SEQ ID NO: 747,359):

>5'UTR OF ENST00000344420|ENSG00000115163_CHR=2_STRAND=FORWARD_UPSTREAM_UTR
-(1260)-ACAACACCCAAGTCCT-(47)-GCCTGAGTGCAGTGGC-(142)-TTCTTCAAAGAAGAAA-(53)-TTTGAGACAGAGTCTC-(9)-CCCAGGCTGGAGTCTG-(1
8)-GGCTCACTACAACCTC-(1)-GCCTCCCAGGTTCAAA-(2)-ATTCTCCTGCCTCAGCCTC-(3)-AGTAGCTGGGATTACAG-(26)-ATAGAGATGGGGTTTC-(6)-TT
GCCAGGCTGGTCT-(2)-AACTCCTGACCTCAGGTGAT-(15)-TCCCAAAGTGCTGGGATTA-(8)-ATTATGTTTCTAAAA-(46)-C
AGACTCCTGCCTCAAA-(237)-GAGTCTTGCTCTGTTG-(3)-CGCTGGAGTGCAGTGG-(9)-GGCTCACTGCAACCTC-(2)-GCTCCCAGGTTCAAGC-(10)-AGTAGC
TGGGACTACAG-(12)-ACATCCGGCTAATTTT-(12)-ATAGAGACGGGGTTTT-(6)-TTGGCCAGGATGGTCT-(4)-CTCCTGACCTCATGATC-(10)-AGCCTCCCAA
AGTGCTGGGG-(4)-AGGCATGAGCCACCACG-(42)-GTCTTGCTCTGTCAC-(14)-TGCAGCCTTGAACTCC-(14)-CCTCCTGCCTCAGCCTCCCGA-(13)-ACAG
GTATGTACCACC (SEQ ID NO: 747,360):

>5'UTR OF ENST00000358820|ENSG00000198037_CHR=12_STRAND=FORWARD_UPSTREAM_UTR
-(504)-AGAGTCTTGCTCTGTCGCCCAGGCTGGAGTGCA-(13)-GGCTCACTGCAACCTC-(1)-GCCTCCCAGGTTCAAG-(2)-ATTCTCCTGCCTCAGCCTC-(3)-T
GTAGCTGGGATTACAGGC-(6)-CACCATGCCCGGCTAAT-(4)-TTATTTTTAGTAGAGA-(15)-TTGGCCAGGCTGGTCT-(2)-AACTCCTGACCTCAGTGAT-(15)-
TCCCAAAGTGCTGGGATTACAGGCCG-(29)-TGCTCTTGCTGTGTCCACCAGGCTGGAGTGCA-(25)-TCTTGAATTCCTGGGC-(19)-AAGCCTC
CCAAGTAGCT-(7)-CAGGCACATACTACCA-(21)-TTTTTGTAGAGACAGG-(4)-TTACTATGTTGCCCAGACTGGTCTTGAACTCC-(41)-ATTACAGGTGTGAGCC
T-(57)-GTTTTTTGAGACAGAGT-(12)-GGCTCACTGCAGCCTC-(13)-GGCTCACTGGGAGTGCA-(13)-GGCTCACTGCAGCCTC-(2)-CCTCCCAAGGCTCAGG-(2)-ATCCTCTTGCCTCAGC-(16)
)-ACCAAGTAGCTGGGAC-(1)-

FIG. 12C

| FIG. 12A |
| FIG. 12B |
| FIG. 12C |

FIG. 12

(SEQ ID NO: 747,361):

>5'UTR OF ENST00000357256|ENSG00000148297_CHR=9_STRAND=REVERSE_UPSTREAM_UTR
-(66)-GGCTGGACGGCAGAGG-(128)-CCCAGGCTGGAGTGCA-(7)-GATCTCGGCTCACTGCG-(24)-ATTCTCCTGCCTCAGCCTC-(3)-AGTAGCTGGGATTACA
G-(7)-CCATCACGCCCGGCTA-(37)-TTGGTCAGGCTAGTCT-(2)-AACTCCTGACCTCAGGTGAT-(13)-TCCCAAAGTGCTGGGATTACAGGCGTGAGCCACCG-
(44)-GCAGAGACTGGAGGGA-(63)-

(SEQ ID NO: 747,362):

>5'UTR OF ENST00000355921|ENSG00000174652_CHR=19_STRAND=REVERSE_UPSTREAM_UTR
-(7)-TCTGTTGCCAGGCTGGAGTGCGTGGTCTTGCTCTGTGATCTCGGCTCACTGCAACCTC-(3)-CTCTCAGGTTCAAGCGATTCTCCTGCCTCAGCCTCAGTAGCT
GGGATT-(3)-AGGCATGCACTACCAT-(25)-TAGAGATGGGGTTTCACCAC-(1)-TTGCCCAGGCTGGTCT-(2)-AACTCCTGACCTCAAC-(19)-TCCCAAAGTGCT
GGGATTACAGGCGTGAGCCACCG-(2)-CCCGGCCTGATTTTT-(257)-CTGGATAAAGAGAATG-(295)-GAGTCTTGCTCTGTTGCTCAGCCTGGAGTGCA-(7)-
GATCTCAGCTCATTGC-(7)-GCCCCCCAGGTTCAAG-(5)-TTCCTGCCTCAGCCTC-(3)-AGTAGCTGGGATTACAG-(12)-ACACCTGGCTAATTT-(5)-ATTTTAG
TAGAGATGG-(12)-TGGCCAGGATGGTCT-(11)-CCTCAAGTGATCTGCCTG-(8)-TCCCAAAGTGCTAGGATTACAGGTGAGCCATCA-(80)-TTCCTTATCT
GTAAA-(156)-GAATGACTTTGGGGTA-(41)-TTCTTTCTTTCCATG-(633)-

(SEQ ID NO: 747,363):

>5'UTR OF ENST00000355587|ENSG00000140264_CHR=15_STRAND=FORWARD_UPSTREAM_UTR
-(255)-ACATATTTTAAATTCT-(1004)-GAGTCTTGCTCTGTTGCCAGGCTGGAGTGCA-(8)-GTCTCAGGTTCACTGCA-(6)-GCCCTCTTGGGTTCAAG-(6)-TCCTA
CCTGCCTCCT-(1)-AGTAGCTGGGATTACAG-(5)-TACCACCATGTCCAGC-(12)-TTTTACTAGAGATGGGGTTT-(7)-TTGGCCAGGCTGGTCT-(4)-CTCCTGA
CCTCATGATC-(14)-TCCCAAAGTGCTGGGATTACAGGCATGAGCCACCG-(253)-GAATGGGCAAAAGCTG-(125)-GTCTTGCTCTGTCACC-(1)-AGGCTAGAG
TGCAGTG-(7)-TTCAGCTCACTGCAACCT-(2)-GCCTCCCGGGTTCAAG-(10)-GCCTCCACCTCCTGAGCAGCTGGGATTACAGG-(7)-CACCATGCCCGGCTAA
T-(34)-TGTTAGCCAGGATTGTCT-(4)-CTCTTGACCTCGTGATC-(14)-TCCCAAAGTGCTGGGATTACAGGCGTGAGCCACTG-(379)-CAATGTTTTACAGTTT-(7
0)-CTGAAGGTTACACAGAGC-(321)-GAGTGTGTGTGAGAGA-(406)-AACCCAGGAGGGTTGAA-(124)-ATCTGACCTTTCTCTC-(214)-TGTGCCAGGCCCAGGG-(3
03)-

(SEQ ID NO: 747,364):

>5'UTR OF ENST00000326880|ENSG00000120662_CHR=13_STRAND=REVERSE_UPSTREAM_UTR
-(101)-TTGTCGCCCACGCTGG-(13)-ATCTCAGTTCACTGCA-(6)-GCCTCCCAGGTTCAAG-(9)-TGCCTCAGCCTCCGA-(2)-AGCTAGGACTACAGGT-(10)-ACG
CTCAGCTAATTT-(18)-GATGGGGTTTCCCAT-(1)-TTGGCCAGGCTGGTCT-(2)-AACTCCTGACCTCAGA-(38)-CAGGCGTGAGCCACTG-(8)-ACATTTGGTAT
GTTT-(282)-TGAACAGGCAACTTACA-(105)-AATAATATTTTCTTCA-(312)-TGCTGGAGTGCAATGG-(9)-GGCTCACTGCAACCTC-(1)-GCCTCCTGGGTTCAGG-
(5)-CTCCTGCCTCAGACTC-(3)-AGTAGCTGGGATTACAG-(2)-GCCTCGCACCACCACGCCCGG-(27)-GTGTTTCACTATGTTG-(3)-GGGCGTGGTCTCGAACT-(1)-CTG
CCCTCAGGTGATC-(14)-TCCCAAAGTGCTGGGATTA-(2)-GGCGTGAGCCACCGCT-(46)-TAGATGAAACAAGATT-(24)-TATGCATGTATCTTA-(7)-TTTTTTTT
AAAGACT-(26)-

FIG. 13A

Note: Amino acid-coding regions for ten genes. The shown coding regions are mosaics composed of the 124 instances of 11 pyknons in various arrangements. It is important to remember that the shown pyknons have 40 or more copies in the genome's intergenic and intronic regions. The string (xx) indicates the number of nucleotides, xx, that separate the surrounding pyknons. To appreciate the importance of this picture it suffices to keep track of the number of copies and relative arrangement of the four pyknons AAATGTGAAGAATGTG (SEQ ID NO: 747,369), TCATACTGGAGAGAAA (SEQ ID NO: 747,366), ACAAGTGTGAAGAATG (SEQ ID NO: 747,367) and CATACTGAAGAGAAAC (SEQ ID NO: 747,368) in each of the shown sequences. All of these genes encode C2H2 type zinc-finger proteins: ENST00000356096 codes for a negative regulator of osteoclast differentiation and is involved in DNA-dependent regulation of transcription; ENST00000357002 encodes a hematopoietic-cell-derived zinc-finger protein that is involved in the negative regulation of transcription from the Pol-II promoter; the products of ENST00000335117 and ENST00000331027 are known to be involved in DNA-dependent transcription regulation.

(SEQ ID NO: 747,369):

>AMINO-ACID CODING REGION OF ENST00000335117||ENSG00000160321_CHR=19_STRAND=REVERSE
-(166)-AAGGAAAAAACCTTT-(74)-AGCAGAGCATAAAAGA-(50)-ATTTACAGTTTAAAAA-(259)-AAATGTGAAGAATGTG-(46)-TCATACTGGAGAGAAA-(90)-AAATGTGAAGAATGTG-(46)-TCATACTGGAGAGAAA-(6)-AAATGTGAAGAATGTG-(68)-AAATGTGAAGAATGTG-(46)-TCATACTGGAGAGAAA-(6)-AAATGTGAAGAATGTG-(68)-AAATGTGAAGAATGTG-(46)-TCATACTGGAGAGAAA-(6)-AAATGTGAAGAATGTG-(130)-TCATACTGGAGAGAAA-(6)-AAATGTGAAGAATGTG-(46)-TCATACTGGAGAGAAA-(66)-

(SEQ ID NO: 747,370):

>AMINO-ACID CODING REGION OF ENST00000331027||ENSG00000182111_CHR=7_STRAND=FORWARD
-(48)-AAATGTGAAGAATGTG-(83)-AAATGTGAAGAATGTG-(46)-TCATACTGGAGAGAAA-(68)-TCATACTGGAGAGAAA-(65)-TCATACTGGAGAGAAA-(90)-AAATGTGAAGAATGTG-(130)-TCATACTGGAGAGAAA-(68)-TCATACTGGAGAGAAA-(6)-AAATGTGAAGAATGTG-(46)-TCATACTGGAGAGAAA-(6)-AAATGTGAAGAATGTG-(80)-AAATGTGAAGAATGTG-(46)-TCATACTGGAGAGAAA-(6)-AAATGTGAAGAATGTG-(46)-TCATACTGGAGAGAAA-(6)-AAATGTAAAGAATGTG-(46)-TCATACTGGAGAGAAA-(6)-AAATGTGAAGAATGTG-

FIG. 13B (SEQ ID NO: 747,371):

>AMINO-ACID CODING REGION OF ENST00000341265||ENSG00000182141_CHR=13_STRAND=REVERSE
-(204)-AAATGTGAAGAATGTG-(46)-TCATACTGGAGAGAAA-(6)-AAATGTGAAGAATGTG-(236)-AAATGTGAAGAATGTG-(47)-CATACTGAAGAGAAAC-(5)-AAATGTGAAGAATGTG-(56)-TGTGAAAAATGTGGCA-(191)-AAATGTGAAGAATGTG-(65)-AAATGTGAAGAATGTG-(68)-AAATGTGAAGAATGTG-(46)-TCATACTGGAGAGAAA-(36)-

(SEQ ID NO: 747,372):

>AMINO-ACID CODING REGION OF ENST00000357002||ENSG00000183850_CHR=19_STRAND=FORWARD
-(93)-AATTTATATAGAAATG-(185)-TCTTTTCAAAAAGCAA-(34)-TTTACAGTTAAGAAAA-(95)-TGATAAATATTTGAAA-(147)-AAATGTAAAGAATGTG-(152)-AAATGTGAAGAATGTG-(46)-TCATACTGGAGAGAAA-(68)-ACAAGTGTGAAGAATG-(50)-ACACTGGAGAGAAACC-(4)-AAATGTGAAGAATGTG-(46)-TCATACTGGAGAGAAA-(152)-ACAAGTGTGAAGAATG-(4)-ACAAGTGTGAAGAATG-(70)-AAATGTGAAGAATGTG-(48)-ACACTGGAGAGAAACC-(4)-AAATGTGAAGAATGTG-(46)-TCATACTGGAGAGAAA-(6)-AAATGTGAAGAATGTG-(47)-CATACTGAAGAGAAAC-(8)-TGTGAAAAATGTGGCA-(43)-TCATACTGGAGAGAAA-(6)-AAATGTGAAGAATGTG-(68)-AAATGTGAAGAATGTG-(158)-

(SEQ ID NO: 747,373):

>AMINO-ACID CODING REGION OF ENST00000330020||ENSG00000184624_CHR=18_STRAND=FORWARD
-(204)-AAATGTGAAGAATGTG-(10)-TAAACAATTCTCAAAA-(20)-TCATACTGGAGAGAAA-(6)-AAATGTGAAGAATGTG-(236)-AAATGTGAAGAATGTG-(47)-CATACTGAAGAGAAAC-(5)-AAATGTGAAGAATGTG-(31)-TCATACTGGAGAGAAA-(9)-TGTGAAAAATGTGGCA-(197)-AAATGTGAAGAATGTG-(47)-CATACTGAAGAGAAAC-(68)-CATACTGAAGAGAAAC-(5)-AAATGTGAAGAATGTG-(46)-TCATACTGGAGAGAAA-(36)-

(SEQ ID NO: 747,374):

>AMINO-ACID CODING REGION OF ENST00000355326||ENSG00000185037_CHR=7_STRAND=REVERSE
-(21)-CAGCCAGAGCCAGGGCA-(232)-AAAGAAACATTTCAAA-(143)-TCATACTGGAGAGAAA-(68)-TCATACTGGAGAGAAA-(90)-AAATGTGAAGAATGTG-(4)-6)-TCATACTGGAGAGAAA-(149)-TCATACTGGAGAGAAA-(174)-AAATGTGAAGAATGTG-(130)-TCATACTGGAGAGAAA-(6)-AAATGTGAAGAATGTG-(152)

FIG. 13C (SEQ ID NO: 747,375):

>AMINO-ACID CODING REGION OF ENST00000356194||ENSG00000196081_CHR=7_STRAND=FORWARD
-(132)-AAATGTGAAGAGAATGTG-(65)-AAATGTGAAGAATGTG-(68)-AAATGTGAAGAATGTG-(130)-TCATACTGGAGAGAAA-(68)-TCATACTGGAGAGAAA-(6
8)-TCATACTGGAGAGAAA-(65)-AATTCATATGAATTG-(9)-AAATGTGAAGAATGTG-(29)-ACTAATCATAAGAGAA-(3)-ACACTGGAGAGAAACC-(4)-AAAT
GTGAAGAATGTG-(68)-AAATGTGAAGAATGTG-(13)-

(SEQ ID NO: 747,376):

>AMINO-ACID CODING REGION OF ENST00000356096||ENSG00000197372_CHR=19_STRAND=REVERSE
-(307)-AAAAATGTGGAAATGA-(130)-TTTAATAAATTTTCAC-(44)-AAATGTAAAGAATGTG-(39)-AAAGAAAATTATACCAA-(94)-AAATGTGAAGAATGTG-(68)-
AAATGTGAAGAATGTG-(152)-AAATGTGAAGAATGTG-(13)-ACACTCCTCAGCCCTT-(19)-ACACTGGAGAGAAACC-(4)-AAA
TGTGAAGAATGTG-(66)-ACAAGTGTGAAGAATG-(70)-AAATGTGAAGAATGTG-(46)-TCATACTGGAGAGAAA-(105)-

(SEQ ID NO: 747,377):

>AMINO-ACID CODING REGION OF ENST00000345030||ENSG00000198153_CHR=7_STRAND=FORWARD
-(21)-CAGCCAGAGCAGGGCA-(232)-AAAGAAACATTTCAAA-(143)-TCATACTGGAGAGAAA-(68)-TCATACTGGAGAGAAA-(90)-AAATGTGAAGAATGTG-(4
6)-TCATACTGGAGAGAAA-(152)-AAATGTGAAGAATGTG-(174)-AAATGTGAAGAATGTG-(130)-TCATACTGGAGAGAAA-(6)-AAATGTGAAGAATGTG-(253)
-TCATACTGGAGAGAAA-(17)-

(SEQ ID NO: 747,378):

>AMINO-ACID CODING REGION OF ENST00000357051||ENSG00000198584_CHR=10_STRAND=REVERSE
-(230)-TTTACAAATAAGAAAA-(174)-AAATGTAAAGAATGTG-(47)-CATACTGAAGAGAAAC-(87)-ACAAGTGTGAAGAATG-(70)-AAATGTGAAGAATGTG-(16
1)-AAATGTGAAGAATGTG-(68)-AAATGTGAAGAATGTG-(47)-CATACTGAAGAGAAAC-(5)-AAATGTGAAGAATGTG-(47)-CATACTGAAGAGAAAC-(10)-TG
AAGAATGTATCAGA-(41)-TCATACTGGAGAGAAA-(30)-

FIG. 13

| FIG. 13A |
| FIG. 13B |
| FIG. 13C |

NOTE: PROBABILITY DENSITY FUNCTION (SOLID LINE) AND THE CORRESPONDING CUMULATIVE (DASHED LINE) FOR THE VARIABLE REPRESENTING THE FRACTION OF THE INSTANCES OF PYKNONS WHICH ARE LOCATED IN REGIONS THAT ARE FREE OF REPEATS.

FIG. 15

| GO TERM | 5' UTR | | CODING | | 3' UTR | |
|---|---|---|---|---|---|---|
| | ENRICHMENT DEPLETION | \|log(p-value)\| | ENRICHMENT DEPLETION | \|log(p-value)\| | ENRICHMENT DEPLETION | \|log(p-value)\| |
| DNA CATABOLISM | 39.54 | 19.88 | | | 89.64 | 23.05 |
| MUSCLE CELL DIFFERENTIATION | 33.85 | 27.11 | 47.16 | 28.08 | | |
| REGULATION OF TRANSCRIPTION, DNA-DEPENDENT | 255.36 | 10.88 | 381.97 | 5.49 | 965.04 | 27.11 |
| REGULATION OF PHYSIOLOGICAL PROCESS | 244.20 | 8.66 | 425.77 | 5.14 | 1096.37 | 22.11 |
| NUCLEO-BASE, SIDE, TIDE, AND NUCLEIC ACID METABOLISM | 290.72 | 11.57 | 1269.93 | 46.78 | 743.14 | 10.27 |
| REGULATION OF METABOLISM | 233.19 | 9.58 | 494.99 | 8.95 | 1018.81 | 27.33 |
| DNA TRANSPOSITION | | | 462.51 | 229.02 | 337.92 | 13.86 |
| DNA METABOLISM | 82.90 | 2.84 | 1219.01 | 155.71 | -316.64 | 8.61 |
| DNA REPLICATION | | | 660.51 | 154.68 | -149.86 | 7.10 |
| MORPHOGENESIS | -117.73 | 3.27 | 287.34 | 4.43 | -488.46 | 9.93 |
| ORGANOGENESIS | -195.48 | 6.58 | -208.11 | 2.34 | -428.31 | 9.26 |
| DEFENSE RESPONSE TO BACTERIA | -27.87 | 4.33 | -94.99 | 10.88 | -185.21 | 34.41 |
| DETECTION OF EXTERNAL STIMULUS | -74.31 | 5.18 | -351.11 | 13.97 | -318.25 | 15.72 |
| ORGANISMAL PHYSIOLOGICAL PROCESS | -136.14 | 3.06 | -607.27 | 15.84 | -616.45 | 11.86 |
| RESPONSE TO EXTERNAL STIMULUS | -156.15 | 7.91 | -725.13 | 34.01 | -694.40 | 23.25 |

NOTE: PARTIAL LIST OF BIOLOGICAL PROCESSES WHOSE CORRESPONDING GENES SHOW SIGNIFICANT ENRICHMENT (LIGHT SHADED CELLS) OR DEPLETION (DARK SHADED CELLS) IN PYKNON INSTANCES IN THEIR 5'UTR, CR OR 3'UTR. ALL SHOWN log(p-values) HAVE BEEN BONFERRONI-CORRECTED. THOSE OF THE TERMS THAT ARE CONSISTENTLY ENRICHED (RESP. DEPLETED) IN ALL THREE REGIONS ARE COLORED LIGHT SHADE (RESP. DARK SHADE).

NOTE: PYKNONS AND THEIR NATURAL BOUNDARIES: PROBABILITY DENSITY FUNCTIONS FOR THE DISTANCE BETWEEN THE STARTING POINTS OF CONSECUTIVE INSTANCES OF THE PYKNONS, SHOWN SEPARATELY FOR EACH OF THE THREE STUDIED REGIONS, NAMELY 5'UTRs, CRs AND 3'UTRs. THE DISTRIBUTIONS ARE TAIL-HEAVY AND ONLY A PORTION OF THEM IS SHOWN. NOTE THE PEAKS AT ABSCISSAS 18, 22, 24, 26, 29, 30 AND 31.

NOTE: PYKNONS AND THEIR NATURAL BOUNDARIES. PROBABILITY DENSITY FUNCTIONS FOR THE NUMBER OF INTERGENIC (TOP) AND INTRONIC (BOTTOM) COPIES OF THE VARIABLE-LENGTH STRINGS DERIVED BY COUNTING THE INSTANCES OF 3'UTR-CONSERVED PYKNONS AFTER HAVING SHIFTED THEM TO THE RIGHT BY d POSITIONS. IN BOTH CASES, THE CURVES THAT CORRESPOND TO d=0 ARE FOR THE PYKNONS IN $P_{3'UTR}$.

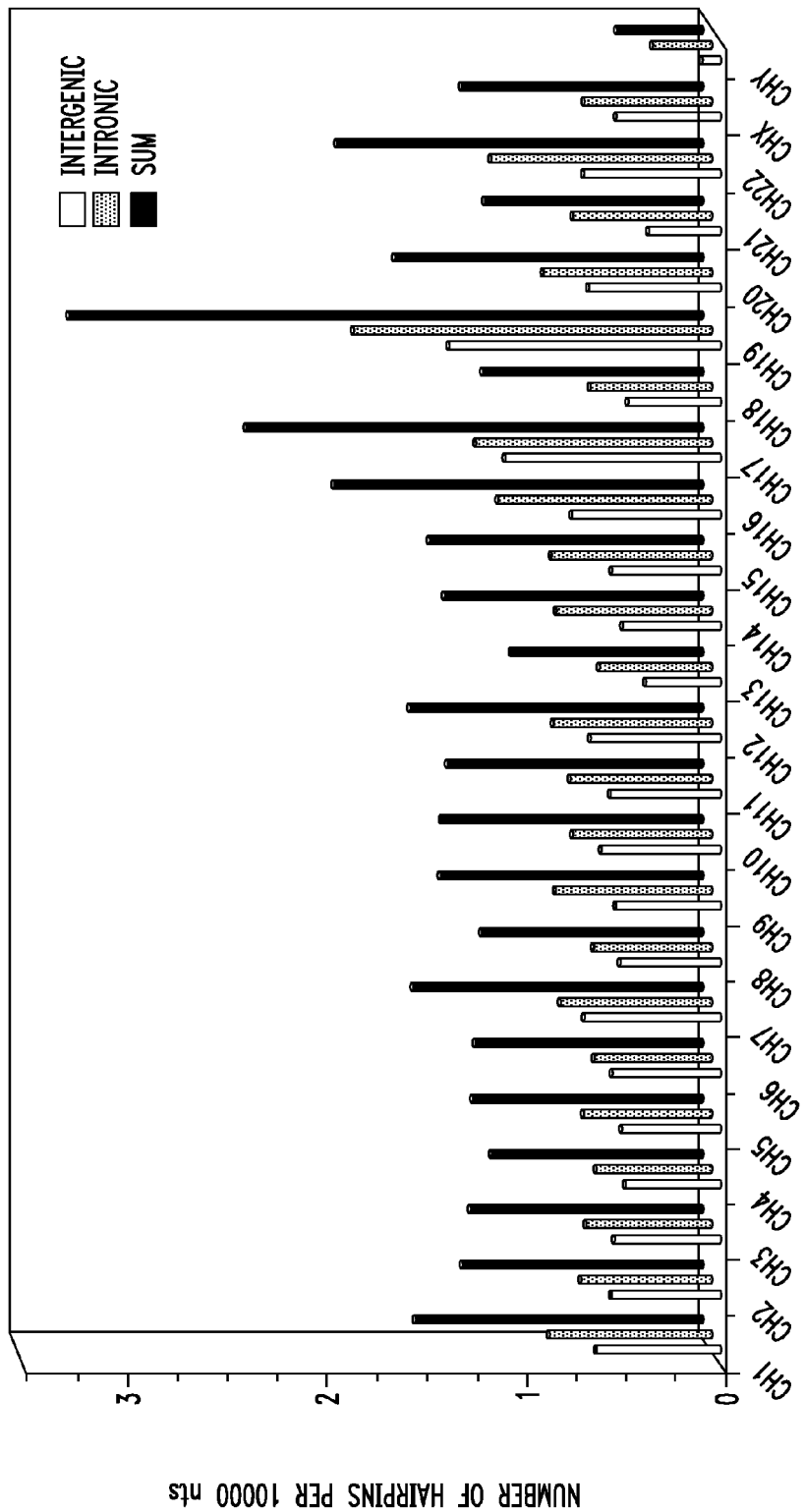

FIG. 18

NOTE: NUMBER OF INTERGENIC/INTRONIC NEIGHBORHOODS, GENERALLY 60 TO 80 NUCLEOTIDES IN LENGTH, EACH OF WHICH CONTAINS THE REVERSE-COMPLEMENT OF A PYKNON AND IS PREDICTED TO FORM DOUBLE-STRANDED, ENERGETICALLY-STABLE, HAIRPIN-SHAPED RNA SECONDARY STRUCTURES – THE NUMBER IS GIVEN PER 10,000 nts OF SEQUENCE. RESULTS ARE SHOWN SEPARATELY FOR EACH CHROMOSOME AND FOR THE INTERGENIC AND INTRONIC REGIONS. THE AVERAGE NUMBER OF HAIRPINS PER 10,000 nts INDEPENDENT OF PROVENANCE IS ALSO SHOWN IN SUM.

FIG. 19

| PATTERN SET/ REGION | POSITIONS COVERED IN CORRESPONDING REGION OF LISTED GENOME PER 10,000 NUCLEOTIDES | | | | | | |
|---|---|---|---|---|---|---|---|
| | HAS | CFA | MMU | RNO | GGA | DME | CEL |
| $P_{5'UTR}$/5'UTR | 382.2 | 43.0 | 20.7 | 14.2 | 9.7 | 22.4 | 5.8 |
| $P_{CODING}$/CODING | 304.1 | 88.3 | 57.4 | 61.1 | 28.4 | 25.2 | 14.7 |
| $P_{3'UTR}$/3'UTR | 733.3 | 152.4 | 82.6 | 64.9 | 42.1 | 65.9 | 57.1 |

NOTE: FOR EACH OF THE THREE REGIONS AND EACH GENOME IN TURN, WE REPORT THE NUMBER OF POSITIONS PER 10,000 NUCLEOTIDES THAT ARE COVERED BY INSTANCES OF THE HUMAN PYKNONS: WE USE THE PATTERNS CONTAINED IN THE SET $P_X$ TO SEARCH REGION X OF THE GENOME X={5'UTR, CODING, 3'UTR} - HSA=HUMAN, CFA=DOG, MMU=MOUSE, RNO=RAT, GGA=CHICKEN, DME=FRUIT-FLY, CEL=WORM.

FIG. 20

| GENOME | NUMBER OF HUMAN PYKNONS WITH ≥ 1 INSTANCE IN THE CORRESPONDING REGION OF LISTED GENOME | | | TOTAL SIZE OF INTERGENIC/INTRONIC REGION (BOTH STRANDS) | INTERGENIC/INTRONIC POSITIONS (BOTH STRANDS) COVERED BY HUMAN PYKNONS | |
|---|---|---|---|---|---|---|
| | $P_{5'UTR}$ | $P_{CODING}$ | $P_{3'UTR}$ | | in nts | per 10,000 nts |
| HSA | 12,267 | 54,396 | 67,544 | 6,093,304,675 | 692,393,548 | 1,136 |
| CFA | 234 | 6,170 | 1,351 | 4,826,002,769 | 87,572,989 | 181.5 |
| MMU | 400 | 8,767 | 6,160 | 5,216,777,897 | 89,568,584 | 171.7 |
| RNO | 170 | 3,424 | 1,644 | 5,409,179,291 | 82,635,080 | 152.8 |
| GGA | 51 | 1,786 | 718 | 1,855,717,211 | 9,262,198 | 49.91 |
| DME | 174 | 1,335 | 1,175 | 228,181,521 | 1,562,508 | 68.5 |
| CEL | 20 | 996 | 790 | 170,879,577 | 1,634,993 | 95.7 |

NOTE: SEEKING INSTANCES OF THE HUMAN PYKNONS IN THE INTERGENIC/INTRONIC REGIONS OF OTHER GENOMES. SEPARATELY FOR SEVEN GENOMES AND FOR EACH 5'UTR, CR AND 3'UTR WE SHOW THE NUMBER OF HUMAN PYKNONS THAT ARE CONSERVED IN THE HUMAN GENOME AND THE CORRESPONDING REGION OF THE j-th GENOME. ALSO, FOR ALL THE PYKNONS WHOSE INSTANCES APPEAR IN COUNTERPART REGIONS OF BOTH THE HUMAN AND THE j-th GENOME, WE SEARCH THE j-th GENOME'S INTERGENIC/INTRONIC REGIONS FOR INSTANCES OF THESE COMMON PYKNONS AND REPORT THE TOTAL NUMBER OF POSITIONS COVERED BY THEIR COPIES; ALSO LISTED IS THE NUMBER OF COVERED POSITIONS PER 10,000 NUCLEOTIDES. HSA=HUMAN, CFA=DOG, MMU=MOUSE, RNO=RAT, GGA=CHICKEN, DME=FRUIT-FLY, CEL=WORM.

RIBONUCLEIC ACID INTERFERENCE MOLECULES AND BINDING SITES DERIVED BY ANALYZING INTERGENIC AND INTRONIC REGIONS OF GENOMES

CROSS-REFERENCE TO RELATED APPLICATIONS

The present application is a continuation-in-part of, and claims priority to, pending U.S. patent application identified as Ser. No. 11/367,512, filed Mar. 3, 2006, and entitled "Techniques for Linking Non-Coding and Gene-Coding Deoxyribonucleic Acid Sequences and Applications Thereof," the disclosure of which is incorporated by reference herein.

FIELD OF THE INVENTION

The present invention relates to genes and, more particularly, to ribonucleic acid interference molecules.

BACKGROUND OF THE INVENTION

It is known that the intergenic and intronic regions comprise most of the genomic sequence of higher organisms. The intergenic and intronic regions are collectively referred to as the "non-coding region" of an organism's genome, as opposed to the "gene-" or "protein-coding region" of the genome. Even though recent work suggested participation of the intergenic and intronic regions in a regulatory role, for the most part, their true function remains elusive. The search for conserved motifs, presumed to be regulatory and control signals, in regions upstream of the 5' untranslated regions (5'UTRs) of genes, has been the focus of research activities for many years.

More recently, researchers began studying the 3' untranslated regions (3'UTRs) of genes where they discovered conserved regions and showed them to be functionally significant, in direct analogy to the cis-motifs of promoter regions. Large-scale comparative analyses allowed researchers to also study conservation in the vicinity of genes and elsewhere in the genome with great success. However, these studies were carried out on only a handful of organisms at a time because of the magnitude of the necessary computations.

The analysis of 3'UTRs intensified further after it was discovered that they contain binding sites that are targeted by short interfering ribonucleic acids (RNAs) that induce the post-transcriptional control of the corresponding gene's expression through either messenger RNA (mRNA) degradation or translational inhibition. Accumulating evidence that non-coding RNAs control developmental and physiological processes and that a considerable part of the human genome is transcribed, has helped researchers identify "functional" elements in areas of the genome that are not associated with protein-coding regions.

SUMMARY OF THE INVENTION

Sequences that can be used in the context of gene regulation are provided. Such sequences may be referred to herein as "pyknon sequences" or simply "pyknons."

In one aspect of the invention, at least one sequence comprising at least one of one or more sequences having SEQ ID NO: 1 through SEQ ID NO: 747,326 is provided. One or more of the provided sequences may be computationally predicted, e.g., from publicly available genomes, using a method based on pattern discovery.

In another aspect of the invention, a method for regulating the expression of a transcript comprises the step of said transcript containing a region that corresponds to at least one of the provided sequences having SEQ ID NO: 1 through SEQ ID NO: 747,326, the region being targeted either by a naturally occurring, or appropriately designed, interfering RNA molecule that regulates the expression of said transcript through post-transcriptional silencing.

In yet another aspect of the invention, a method for regulating the expression of a transcript comprises the step of at least one of the provided sequences having SEQ ID NO: 1 through SEQ ID NO: 747,326 being used to design an interfering RNA molecule that contains a region that corresponds to the reverse complement of one or more of the one or more sequences having SEQ ID NO: 1 through SEQ ID NO: 747,326, the interfering molecule regulating, through post-transcriptional silencing, one or more transcripts that contain said sequence of the one or more sequences having SEQ ID NO: 1 through SEQ ID NO: 747,326, or a substantial fraction thereof.

A more complete understanding of the present invention, as well as further features and advantages of the present invention, will be obtained by reference to the following detailed description and drawings.

BRIEF DESCRIPTION OF THE DRAWINGS

FIG. 3 is a diagram illustrating a probability density function for a number of 16-mers with a given number of copies in a random input set, according to an embodiment of the present invention;

FIG. 4 is a diagram illustrating a preprocessing methodology, according to an embodiment of the present invention;

FIG. 5 is a diagram illustrating pattern specificity and number of appearances, according to an embodiment of the present invention;

FIG. 6 is a diagram illustrating a process for determining logically distinct patterns, according to an embodiment of the present invention;

FIG. 11 is a diagram illustrating combinatorial arrangements of pyknons in 3'UTRs, according to an embodiment of the present invention;

FIG. 12 is a diagram illustrating combinatorial arrangements of pyknons in 5'UTRs, according to an embodiment of the present invention;

FIG. 13 is a diagram illustrating combinatorial arrangements of pyknons in amino acid-coding regions, according to an embodiment of the present invention;

FIG. 15 is a diagram illustrating a partial list of biological processes whose corresponding genes show significant enrichment or depletion in pyknon instances in their 5'UTRs, CRs or 3'UTRs, according to an embodiment of the present invention;

FIG. 18 is a diagram illustrating the number of intergenic/intronic neighborhoods each of which contains the reverse complement of a pyknon and is predicted to fold into a hairpin-like structure, according to an embodiment of the present invention;

FIG. 19 is a diagram illustrating the number of positions per 10,000 nucleotides that human pyknons cover in other genomes, according to an embodiment of the present invention;

FIG. 20 is a diagram illustrating the number of human pyknons that can be found in the untranslated and coding regions of other genomes, and the number of intergenic/intronic positions that human pyknons cover in other genomes, according to an embodiment of the present invention;

DETAILED DESCRIPTION OF PREFERRED EMBODIMENTS

Figure 1:
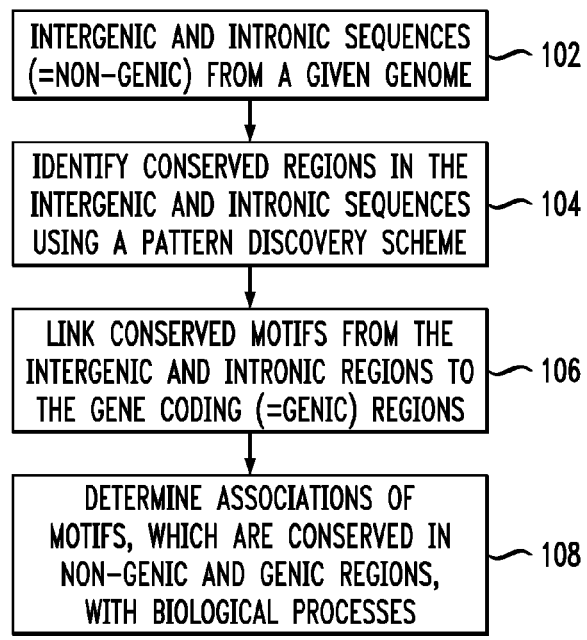
FIG. 1 is a diagram illustrating an exemplary methodology for determining associations between non-coding and gene coding sequences in a genome of an organism, according to an embodiment of the present invention.

FIG. 1 is a diagram illustrating exemplary methodology 100 for determining associations between non-coding and gene coding sequences in a genome of an organism. In step 102, non-coding sequences from the genome of an organism are obtained. Preferably, the non-coding sequences comprise intergenic and/or intronic sequences. As used herein, the term "intergenic" refers generally to any portion of a deoxyribonucleic acid (DNA) strand that is between gene sequences. Further, as used herein, the term "intronic" refers to any portion of a DNA strand that is encompassed by an intron.

According to one exemplary embodiment, the genome comprises the human genome. Further, as will be described below, the starting point of the present techniques may be the genome of a single organism, e.g., the human genome.

In step 104, conserved regions in the intergenic/intronic sequences are identified. As will be described in detail below, these conserved regions may be identified by used pattern discovery techniques to identify patterns existing in the sequences.

In step 106, the identified conserved regions (also referred to as 'conserved motifs') of the intergenic/intronic non-coding sequences are linked to gene coding regions of the genome. Specifically, instances of the patterns, described, for example, in conjunction with the description of step 104, above, may be searched for in gene coding regions of the genome. For example, as will be described in detail below, sequences will be identified, e.g., that are at least 16 nucleotide bases in length and appear a minimum of 40 times in the non-coding region of a genome, and which also appear at least one time in the coding region of the genome. These identified sequences (motifs) link the coding and non-coding regions of the genome. As will also be described in detail below, linking the conserved regions and gene coding regions of the genome provides for an association to be made with the biological processes of the organism.

In step 108, as will be described in detail below, the identified motifs that link the non-genic and genic regions of a genome also provide for an association between these motifs and specific biological processes that even persists in organisms beyond the human genome.

As used herein, the phrase "conserved region" may also be referred to as a "conserved motif" or a "conserved block" or "an exceptionally-well-conserved block (EWCB)" or a "pyknon." The term "pyknon" is from the Greek adjective πυκνός/πυκνή/πυκνόν meaning "serried, dense, frequent."

Accordingly, using an unsupervised pattern discovery method, we processed the human intergenic and intronic regions and catalogued all variable-length patterns with identically conserved copies and multiplicities above what is expected by chance. Among the millions of discovered patterns, we found a subset of 127,998 patterns, termed pyknons, which have one or more additional non-overlapping instances in the untranslated and protein-coding regions of 30,675 transcripts from 20,059 human genes. The pyknons are found to arrange combinatorially in the 5' untranslated, coding, and 3' untranslated regions of numerous human genes where they form mosaics. Consecutive instances of pyknons in these regions exhibit a strong bias in their relative placement favoring distances of about 22 nucleotides. We also found that pyknons are enriched in a statistically significant manner in genes involved in specific processes, e.g., cell communication, transcription, regulation of transcription, signaling, transport, etc. For about $1/3^{rd}$ VP of the pyknons, the intergenic/intronic instances of their reverse complement lie within 382,244 non-overlapping regions, typically 60-80 nucleotides long, which are predicted to form double-stranded, energetically stable, hairpin-shaped RNA secondary structures; additionally, the pyknons subsume about 40% of the known microRNA sequences, thus suggesting a possible link with post-transcriptional gene silencing and RNA interference. Cross-genome comparisons revealed that many of the pyknons are also present in the 3'UTRs of genes from other vertebrates and invertebrates where they are over-represented in similar biological processes as in the human genome. These novel and unexpected findings suggest potential functional connections between the coding and non-coding parts of the human genome.

Thus, in accordance with an illustrative methodology of the invention, we examine whether highly specific patterns exist within a single genome that may act as targets or sources for such putative regulatory activity or as a 'vocabulary' for yet undiscovered mechanisms. Our analysis represents a substantial point of departure from previous efforts. First, we carry out all of the analysis on a single genome. Second, we seek patterns in the intergenic and intronic regions of the genome (not the UTRs or protein coding) regions. Third, the pattern instances transcend chromosomal boundaries. And, fourth, we rely on the unsupervised discovery of conserved motifs instead of searching schemes. In particular, we sought to discover identically conserved, variable-length motifs of certain minimum length but unlimited maximum length in human intergenic and intronic regions. We discovered more than 66 million motifs with multiplicities well above what is expected by chance. A sizeable subset of these motifs, referred to as the pyknons, have one or more additional instances in the untranslated and coding regions of almost all known human genes and exhibit properties that suggest the possibility of an extensive link between the non-genic and genic regions of the genome and a connection with post-transcriptional gene silencing (PTGS) and RNA interference (RNAi).

Figure 2:
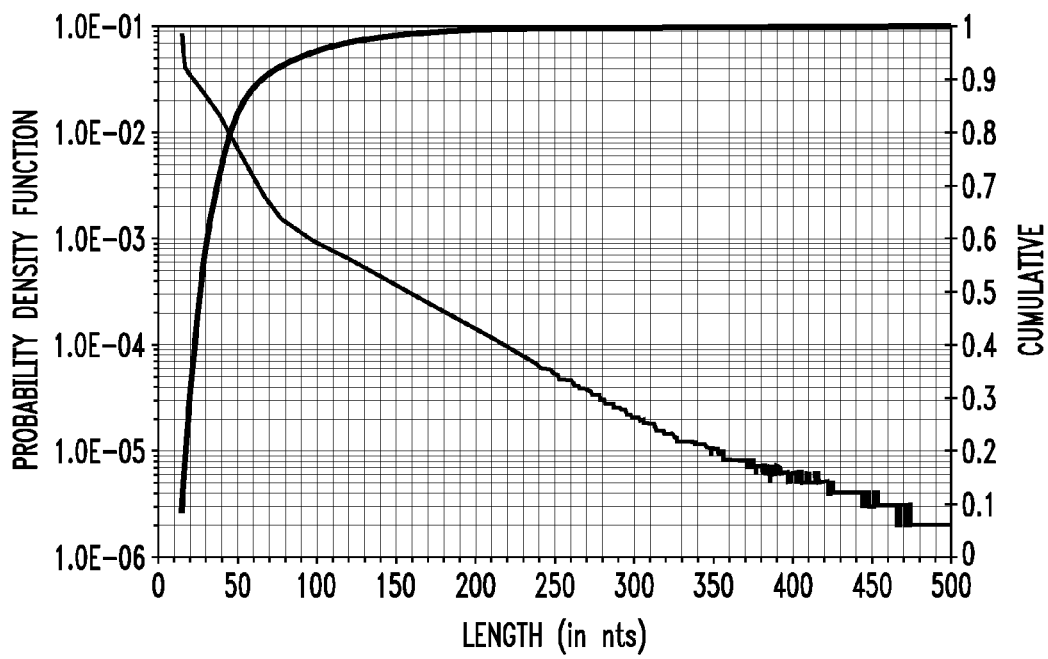
FIG. 2 is a diagram illustrating a probability density function and a cumulative distribution for lengths of patterns discovered in analyzed intergenic and intronic sequences of the human genome, according to an embodiment of the present invention.

As described, for example, in conjunction with the description of step 104 of FIG. 1, above, according to the techniques described herein, a pattern discovery step may be performed. We used the parallel version of a pattern discovery algorithm described in I. Rigoutsos et al., *Combinatorial Pattern Discovery in Biological Sequences: the TEIRESIAS Algorithm*, 14 BIOINFORMATICS 1, pgs. 55-67 (Jan. 1998) (hereinafter "Rigoutsos"), the disclosure of which is incorporated by reference herein. The pattern discovery (Teiresias) algorithm seeks variable-length motifs that are identically conserved across all of their instances, comprise a minimum of L=16 nucleotides and appear a minimum of K=40 copies in the processed input (see below regarding the values of L, K). The algorithm guarantees the reporting of all composition-maximal and length-maximal patterns satisfying these parameters. The input comprised the intergenic and intronic sequences (step 102 of FIG. 1) of the human genome from ENSEMBL Rel. 31 (see Stabenau, A., McVicker, G., Melsopp, C., Proctor, G., Clamp, M. & Birney, E. (2004) *Genome Res* 14, 929-33) for a total of 6,039,720,050 nucleotides. The input did not include the reverse complement of the 5' untranslated, amino acid coding or 3' untranslated regions of any human genes. This exclusion ensures that any discovered patterns are not connected in any way to sequences of known genes, protein motifs or domains. The algorithm ran on a shared-memory architecture with 128 Gigabytes of main memory and 8 processors running at a clock frequency of 1.75 GHz, and generated an initial set $P_{init}$ of 66+ million statistically significant patterns (see below). Most of the patterns in $P_{init}$ were a few tens of nucleotides in length. FIG. 2 shows the probability density function (in black) and cumulative distribution (in light gray) for the lengths of the more than 66 million patterns discovered in the analyzed intergenic and intronic sequences of the human genome. These patterns form the set $P_{init}$. As can be seen from FIG. 2, more than 95% of all discovered patterns are shorter than 100 nucleotides. Note that the primary Y-axis is logarithmic whereas the secondary is linear.

The Teiresias discovery algorithm that we used for this analysis requires the setting of three parameters: L, W and K. The parameter L controls the minimum possible size of the discovered patterns but has no bearing on the patterns' maximum length; the latter is not constrained in any way. The parameter W satisfies the inequality $W \geq L$ and controls the 'degree of conservation' across the various instances of the reported patterns: smaller (respectively, larger) values of W will tolerate fewer (respectively, more) mismatches across the instances. Since for this analysis, we are interested only in patterns with identically conserved instances, we set W=L (i.e., the patterns contained no "wild cards"). Finally, the parameter K controls the minimum required number of appearances before a pattern can be reported by the algorithm.

For a given choice of L, W and K, the algorithm guarantees the reporting of all patterns that have K or more appearances in the processed input and are such that any L consecutive (but not necessarily contiguous) positions span at most W positions. These patterns are generally overlapping: a given sequence location can simultaneously appear in multiple, distinct, non-redundant patterns. It is also important to stress three properties of the algorithm. First, as stated above, the value L does not impose any constraint on the maximum length of a pattern which is unbounded. Second, each reported pattern will be maximal in composition, i.e., it cannot be made more specific by specifying the value of a wildcard without decreasing the number of locations where it appears. And, third, each reported pattern will be maximal in length, i.e., it cannot be made longer without decreasing the number of locations where it appears. In this discussion, we use the terms pattern, block and motif interchangeably.

Opting for small L values generally permits the identification of shorter conserved motifs that may be present in the processed input, in addition to all longer ones—see above properties. Generally, for short motifs to be claimed as statistically significant they need to have a large number of copies in the processed input; requiring a lot of copies runs the risk of discarding bona fide motifs. On the other hand, larger values of L will generally permit the identification of statistically significant motifs even if these motifs repeat only a small number of times. This happens at the expense of significant decreases in sensitivity; i.e. bona fide motifs will be missed.

For our analysis, we have selected L=16, a value that strikes a balance between the desirable sensitivity (which favors lower L values) and achievable specificity (which favors higher L values). We stress that the maximality properties of the pattern discovery step ensure that we will be able to report any and all motifs that are 16 nucleotides or longer. And as explained above, we will set W=L.

The last parameter that needs to be set is K, the required number of appearances for a pattern to be reported. K needs to be set to a value that can ensure that the reported patterns could not have been derived from a random database with the same size as the input at hand. In order to determine this value, we used several randomly-shuffled versions of our intergenic and intronic input (of approximately 6 billion bases) and in there sought frequent, fixed-size 16-mers with all low-complexity 16-mers removed by NSEG (see Wootton, J. C. & Federhen, S. (1993) *Computers in Chemistry* 17, 149-163). The idea here is that if a randomly-shuffled version of our input set cannot give rise to any 16-mers that appear more than $K_X$ times, then it will also be true that no patterns exist in the input set that are longer than 16 nucleotides and have more than $K_X$ copies. Several iterations of this process allowed us to establish that $K_X$=23. FIG. 3 shows the probability density function for the number of 16-mers with a given number of copies in the random input set—note that both the X and Y axes are logarithmic. From this, it follows that a randomly-shuffled version of our input set cannot possibly give rise to patterns which are longer than 16 nucleotides and have more than 23 copies: in fact, as a pattern increases in length, the number of times it appears in a given input set can only decrease. We thus opted for the even larger threshold of K=40 for our pattern discovery step.

Before we sought to discover patterns in the intergenic and intronic regions of the human genome, we preprocessed the sequences and removed: a) all the regions that corresponded to 5' untranslated, coding and 3' untranslated regions of known genes; and, b) all the regions that were the reverse complement of 5' untranslated, coding and 3' untranslated regions of known genes. We show this preprocessing step pictorially in FIG. 4. The genomic input before the preprocessing step is shown above the arrow, and the input upon which pattern discovery is run is shown below the arrow.

Under the assumption that all four nucleotides are equiprobable (i.e., $p_A=p_T=p_C=p_G=\frac{1}{4}$), independent, and, identically distributed, we estimate the probability p of a pattern of length l to be $p=4^{-l}$. We can compute the probability $Pr_k$ to observe k instances of a given pattern in a database of size D (D>>1) to be $Pr_k \approx (pD)^k e^{-pD}/k!$ (Poisson distribution). The least specific pattern that our method will discover is one that is the shortest possible (i.e., l=L=16) and appears the smallest allowed number of times (i.e., k=K=40): if D=6.0× $10^9$ bases (=all chromosomes and both strands), then $Pr_k=1.95\times 10^{-43}$.

We now revisit this calculation by taking into account the nucleotides' natural probability of occurrence. Using ENSEMBL Release 31 from May 2005 (based on NCBI Assembly 35 from July 2004) as our database D, we see that the fraction of bases that are undetermined across the 24 human chromosomes ranges from roughly 1.2 to 61.0% for the Y chromosome. Of course, the following constraints should apply: $p_A=p_T$ and $p_C=p_G$. Since the fractions of nucleotides that are undetermined are not equal, the required balance between A/T and C/G is only approximately preserved. Ignoring the unspecified positions and recomputing ratios based on the remaining bases, we find that $p_A=p_T\approx 3/10$ and $p_C=p_G\approx 2/10$.

Let us consider a block of size 1 and let "match" indicate the match between the i-th character of this block and a character c at position in a database D of nucleotide sequences. Then it is easy to see that:

$$Pr(\text{match}) = Pr(\text{match with } c)$$
$$= Pr(\text{match} \wedge (c \text{ is one of } A, C, G, T))$$
$$= Pr((\text{match} \wedge c = A) \vee (\text{match} \wedge c = C) \vee (\text{match} \wedge c = G) \vee (\text{match} \wedge c = T))$$
$$= Pr(\text{match} | A)Pr(A) + Pr(\text{match} | C)Pr(C) + Pr(\text{match} | G)Pr(G) + Pr(\text{match} | T)P(T)$$
$$= Pr(A)Pr(A) + Pr(C)Pr(C) + Pr(G)Pr(G) + Pr(T)P(T)$$
$$= Pr(A)^2 + Pr(C)^2 + Pr(G)^2 + Pr(T)^2$$
$$= p_A^2 + p_C^2 + p_G^2 + p_T^2$$
$$= 0.3^2 + 0.3^2 + 0.2^2 + 0.2^2$$
$$= 0.26$$

In this analysis, we consider blocks of length l with $l \geq 16$. Naturally, these shortest blocks will be associated with the largest probability p of observing a pattern accidentally—the value p decreases as the value of l increases. The probability that a block of length l=16 will have one instance in the database D is then $p_1 \triangleq Pr(\text{match})^{16} = (0.26)^{16}$ or $p_1=4.4*10^{-10}$.

An alternative way to approach this is to assume that the block of length l is constructed by drawing from the same nucleotide distribution that gives rise to the database D. Then, a block of length l=16 would comprise $p_A*16\approx 5$ A's, $p_C*16\approx 3$ C's, $p_G*16 \approx 3$ G's and $p_T*16\approx 5$ T's. Then, the probability that this block will arise accidentally is $p_2 \triangleq p_A^5 * p_C^3 * p_G^3 * p_T^5 = 3.8*10^{-10}$.

We can compute the probability of finding k accidental instances in a database D that contains $6\times 10^9$ bases where each of the instances is independent of all the preceding instances using the Poisson distribution $Pr_k \approx (pD)^k e^{-pD}/k!$. The probability $Pr_k$ that a 16-mer will appear k times with k=40 is equal to $4.5*10^{-33}$ (resp. $2.6*10^{-35}$) if $p_1$ (resp. $p_2$) is used in the calculation.

We thus can see that even if we take into account the natural frequency of appearance in the human genome of each of the four nucleotides, the probability that one of our discovered blocks is accidental remains very small even for blocks of size 16 that appear only 40 times.

Alternatively, we can estimate the significance of our patterns using z-scores: for the least specific patterns of length 16 that have exactly 40 identical copies we obtain the remarkably-high value of z=32.66. Longer patterns and patterns with more intergenic/intronic copies have even higher z-scores. These analyses confirm in different ways that every one of our discovered patterns is statistically significant and not the result of a random process. These conclusions hold true for the reverse complements of the discovered patterns as well and for the pyknons that are a subset of the discovered patterns $P_{init}$.

It is to be noted that we will use the terms "coding" and "coding region" (abbreviated as CR and CRs) to refer to the translated, amino-acid coding part of exons.

We now describe the step of determining which of the discovered patterns have additional instances in the 5'UTRs, CRs or 3'UTRs of known genes. Once the pattern discovery step has produced the set $P_{init}$ of variable length patterns, we processed it to identify 'logically distinct' patterns using the following approach. Let there be a recurrent logical unit which appears several times in the intergenic/intronic regions of the human genome; each one of its instances is assumed to have different lengths that reflect varying degrees of conservation. For simplicity, we assume here that different degrees of conservation will result in variable length instances of the pattern. We only seek patterns with identically-conserved instances so this is a correct assumption. For example's sake, we will assume that all variations of the logical unit contain an intact copy of an 18-nucleotide core motif; let TCCCATAC-CACGGGGAT (SEQ ID NO: 747,327) represent this core. As the instances of the logical unit become longer and thus more specific, the number of appearances in the input decreases. FIG. 5 shows this example in more detail. Several hypothetical variations of the logical unit are aligned around the common core motif and the number of instances is listed next to each variation.

We reasoned that these patterns should be processed in order of decreasing value of the total number of positions that they span: this number is simply the product of each pattern's length by the number of times it appears in the input. As patterns are examined in turn, some of them are selected and kept whereas others collide with earlier-made selections.

Two collision scenarios are possible and we examine them with the help of FIG. 6. Two blocks, light and darker gray, are shown therein together with a 'reference set' of sequences. The light gray block corresponds to a pattern that has already been examined and placed at all its instances. The instances of the darker gray block show the intended placements for the pattern currently under consideration. The blocks collide at two locations (they overlap in the first and second sequence) but the rest of their instances are disjoint. We have two possibilities regarding the handling of collisions. The darker gray block is kept if and only if there is at least one other location in the reference sequence set where it can be placed without generating a collision (e.g. the fifth and sixth sequences in FIG. 6). Alternatively, the darker gray block is kept if and only if it generates no collisions whatsoever with any block that has already been selected and placed. We have opted for the stricter, second choice: if a pattern's instance uses a position that has already been claimed by an earlier-selected pattern, then the pattern under consideration will be discarded and not considered further. Generally, it will be redundant variations of the same pattern that will generate collisions: only one pattern will be used to represent a core motif such as the one shown in FIG. 5.

The one remaining element is to decide which sequences to use as the reference set. We have chosen to use each of the 5'UTRs, CRs, and 3'UTRs in turn. Sub-selecting among the patterns in $P_{init}$ with the help of each of the 5' untranslated, coding and 3' untranslated regions gives rise to the pattern collections $P_{5'UTR}$, $P_{CODING}$ and $P_{3'UTR}$ respectively. The union of these sets, $P_{5'UTR} \cup P_{CODING} \cup P_{3'UTR}$ comprises the pyknons, i.e., patterns that were originally discovered in the intergenic and intronic regions of the human genome and which have additional instances in the 5' untranslated, coding and 3' untranslated regions of known human genes.

We used the above steps to determine which of the discovered patterns has additional instances in the untranslated and coding regions of genes. After filtering the surviving patterns for low-complexity with NSEG (Wootton, J. C. & Federhen, S. (1993) *Computers in Chemistry* 17, 149-163), we generated three patterns sets $P_{5'UTR}$, $P_{CODING}$ and $P_{3'UTR}$ that contained 12,267, 54,396 and 67,544 patterns respectively and had additional instances in 5'UTRs, CRs and 3'UTRs. The union of $P_{5'UTR} \cup P_{CODING} \cup P_{3'UTR}$ contained 127,998 patterns indicating that the three pattern sets are largely disjoint. We refer to these 127,998 patterns as pyknons.

Figure 7:
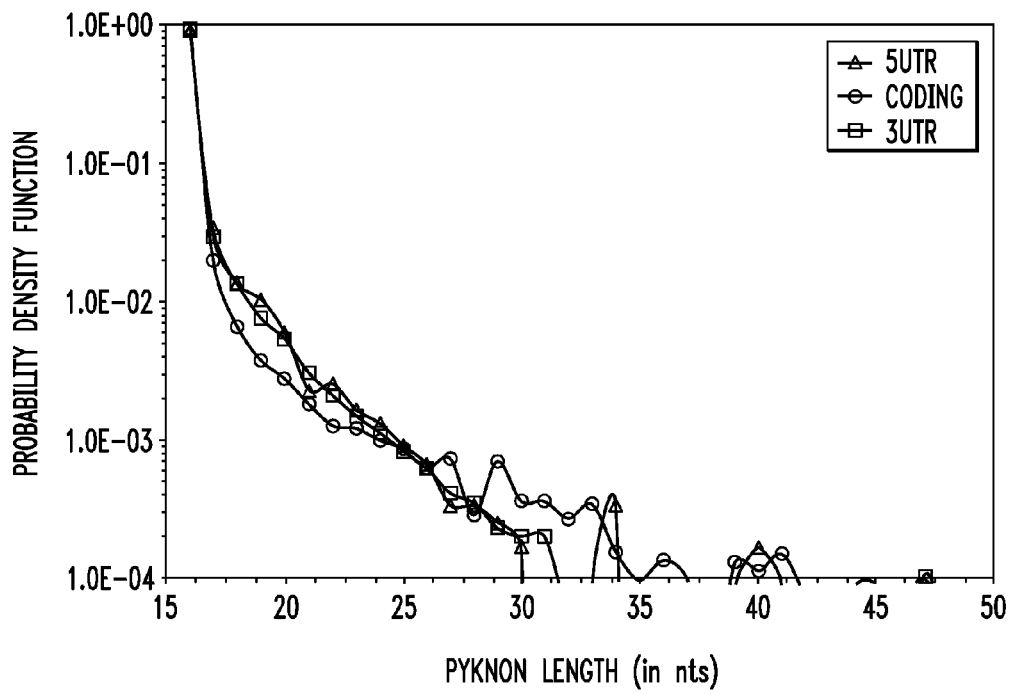
FIG. 7 is a diagram illustrating a probability density function for lengths of pyknons, according to an embodiment of the present invention.

We know describe some properties of the pyknons. The three patterns sets $P_{5'UTR}$, $P_{CODING}$ and $P_{3'UTR}$ contain 12,267, 54,396 and 67,544 blocks respectively. The union $P_{5'UTR} \cup P_{CODING} \cup P_{3'UTR}$ comprises the 127,998 pyknons. In FIG. 7, we show the probability density function for the length of the pyknons; the function is shown separately for each of the three subsets that make up the pyknon collection. Note that the Y-axis is logarithmic.

The patterns in each of the three collections, $P_{5'UTR}$, $P_{CODING}$ and $P_{3'UTR}$, fall into one of two types. "Type-A" patterns are patterns whose reverse complement is also present in the same collection (note that reverse palindromes are included among the type-A patterns). "Type-B" patterns are patterns whose reverse complement is absent from the collection. The breakdown for each of $P_{5'UTR}$, $P_{CODING}$ and $P_{3'UTR}$ is as follows: $P_{5'UTR}$ contains 217 type-A blocks and 11,835 type-B blocks; $P_{CODING}$ contains 1,038 type-A blocks and 52,330 type-B blocks; and $P_{3'UTR}$ contains 2,501 type-A blocks and 62,577 type-B blocks. The clear majority of the blocks in each of the three collections are type-B blocks.

Figure 8:
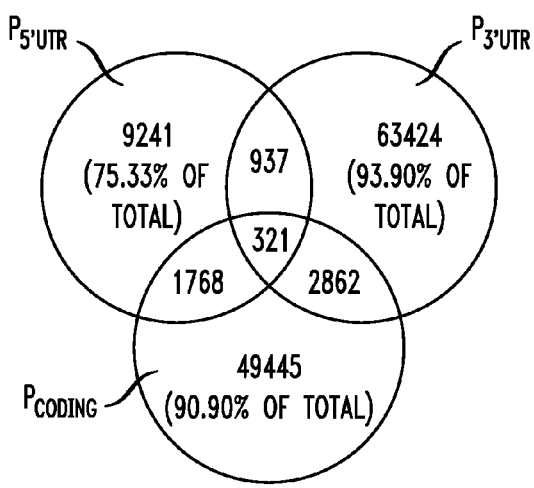
FIG. 8 is a diagram illustrating a number of blocks that are shared by three sets whose union makes up a pyknon collection, according to an embodiment of the present invention.

With respect to their content, the three collections are largely disjoint, a characteristic that presumably reflects sequence differences that are inherent to the actual 5'UTRs, CRs and 3'UTRs. FIG. 8 shows pictorially the relationship among the members of the three sets $P_{5'UTR}$, $P_{CODING}$ and $P_{3'UTR}$: note the small cardinalities of the various intersections.

Figure 9:
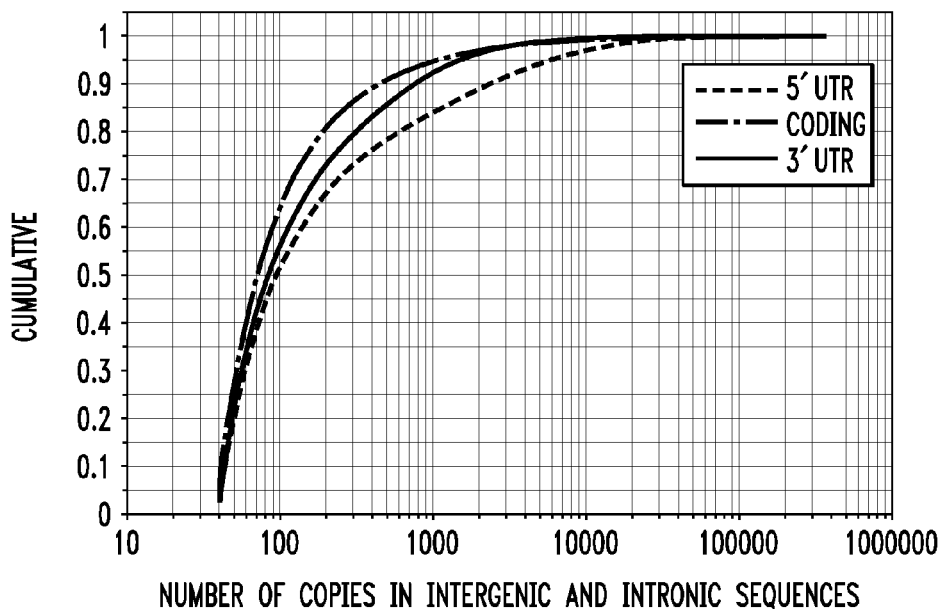
FIG. 9 is a diagram illustrating a cumulative function for a number of intergenic and intronic copies of pyknons, according to an embodiment of the present invention.

Finally, we comment on the number of intergenic and intronic copies of a pyknon. This number spans a very wide range of values with the most frequent pyknon having 356,989 copies—the minimum number of copies is, by design, equal to K=40. For about 95% of the pyknons, their intergenic/intronic copies are fewer than 2,000. FIG. 9 shows the cumulative distributions for the number of intergenic and intronic copies of the pyknons—the distribution is again shown separately for each of $P_{5'UTR}$, $P_{CODING}$ and $P_{3'UTR}$ in order to highlight the similarities and differences of the three sets.

Figure 10:
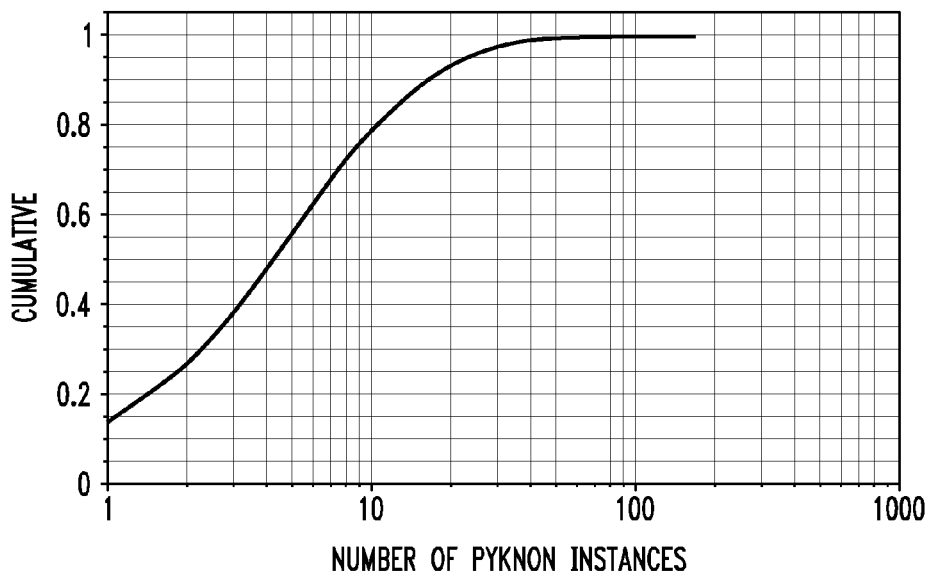
FIG. 10 is a diagram illustrating a cumulative function showing what percentage of affected transcripts contain N or more pyknon instances, according to an embodiment of the present invention.

The pyknons also exhibit a number of properties that connect the non-genic and genic regions of the human genome, as well as other genomes, in unexpected ways. In particular:

The pyknons have one or more instances within nearly all known genes. The 127,998 pyknons that we originally discovered in the human intergenic and intronic regions have an additional 226,874 non-overlapping copies in the 5'UTRs, CRs or 3'UTRs of 20,059 genes (30,675 transcripts). That is, more than 90% of all human genes contain one or more pyknon instances. The pyknons in $P_{5'UTR}$ cover 3.82% of the 6,947,437 nucleotides in human 5'UTRs; the pyknons in $P_{CODING}$ cover 3.04% of the 50,737,024 nucleotides in human CRs; and, the pyknons in $P_{3'UTR}$ cover 7.33% of the 25,597,040 nucleotides in human 3'UTRs. The distribution of pyknons in the various transcripts is not uniform. FIG. 10 shows the cumulative for the number of transcripts with a given number of pyknons instances in them. As can be seen, about 52% of the 30,675 affected transcripts contain four or more pyknon instances; of these about 2,200 transcripts contain 20 or more pyknon instances in them.

The pyknons arrange combinatorially in many human 5'UTRs, CRs and 3'UTRs forming mosaics. In those cases where we find many pyknons in one transcript, the pyknons arrange combinatorially and form mosaics. FIG. 11 shows an example of such a combinatorial arrangement in the 3'UTRs of birc4 (an apoptosis inhibitor) and nine other human genes. The 3'UTR of birc4 contains 100 instances of 95 distinct pyknons: of these, 22 are also present in the 3'UTRs of the other nine genes shown. One or more instances of the 95 pyknons from birc4's 3'UTR exist in the 3'UTRs of 2,306 transcripts (data not shown).

We next show two more examples, one involving 5' untranslated and the other involving coding regions. It is important to stress here that the pyknons are initially discovered in an input that includes neither untranslated/amino-acid-coding sequences nor their reverse-complement; thus, pyknon arrangements such as the ones shown in the following two examples represent non-trivial findings from the standpoint of statistical significance. FIG. 12 shows an example of combinatorial rearrangement in the 5'UTRs of ENSG00000196809 a gene of unknown function and 8 more human genes. 63 distinct pyknons have a total of 65 instances in the 5'UTR of ENSG00000196809. Of the 63 pyknons in the 5'UTR of ENSG00000196809, nine are also shared with the remaining eight genes of the shown group.

FIG. 13 shows an example of combinatorial rearrangement in human coding regions with the help of the amino-acid-coding sequences from 10 distinct genes: 9 pyknons have a total of 124 instances in the coding regions of the shown transcripts with several of the conserved pyknons appearing twice or more in a given sequence.

Recall that we initially discovered the pyknons in an input that included neither transcribed gene-related sequences nor their reverse-complement. Thus, finding so many pyknons with instances in human 5'UTRs, CRs and 3'UTRs is significant, especially in view of the three striking examples of combinatorial rearrangements shown above.

The pyknons account for $\frac{1}{6}^{th}$ of the human intergenic and intronic regions. The intergenic and intronic copies of the pyknons span 692,393,548 positions on the forward and reverse strands. For those pyknons whose reverse complements are not already in the list of 127,998 pyknons, their Watson-strand instances impose constraints on their Crick-strand instances. Considering this and recalculating shows that 898,424,004 positions, i.e., about $\frac{1}{6}^{th}$ of the human intergenic/intronic regions, are covered by pyknons and their reverse complement.

The pyknons are non-redundant. We clustered the pyknons using a scheme based on BLASTN (Altschul, S. F., Gish, W., Miller, W., Myers, E. W. & Lipman, D. J. (1990) *J Mol Biol* 215, 403-10). Two pyknons are redundant if they agree on at least X % of their positions. Since our collection includes pyknon pairs whose members are the reverse complement of one another, we had to ensure that the clustering scheme did not over-count: when comparing sequences A and B, we examined for redundancy the pair (A,B) and the pair (reverse-complement-of-A,B). Clustering at X=70, 80 and 90%, we generated clusters with 32621, 44417 and 89159 pyknons respectively. The high numbers of surviving clusters show that the pyknons are largely distinct.

We next describe the BLASTN-based clustering scheme. Let us assume that we are given a set of N sequences of nucleic acids of variable length, and a user-defined threshold X for the permitted, maximum remaining pair-wise sequence similarity. Then, we carry out the following steps:

```
sort the N sequences in order of decreasing length ;
let S_i denote the i-th sequence of the sorted set ;
let S_l be the longest sequence of the sorted set ;
CLEANED_UP_SET ← S_l
for i = 2 through N do
    use S_i as query to run BLAST against the current contents of CLEAN
    if the top BLAST hit T agrees with S_i or with the reverse complement
    of S_i at more than X% of T 's positions
    then
        make S_i a member of the cluster represented by T ;
        discard S_i ;
    else
        CLEANED_UP_SET ← CLEANED_UP_SET U { S_i } ;
end-for-loop
```

Upon termination, the set CLEANED_UP_SET contains sequences no pair of which agrees on more than X % of the positions in the shorter of the two sequences.

Figure 14:
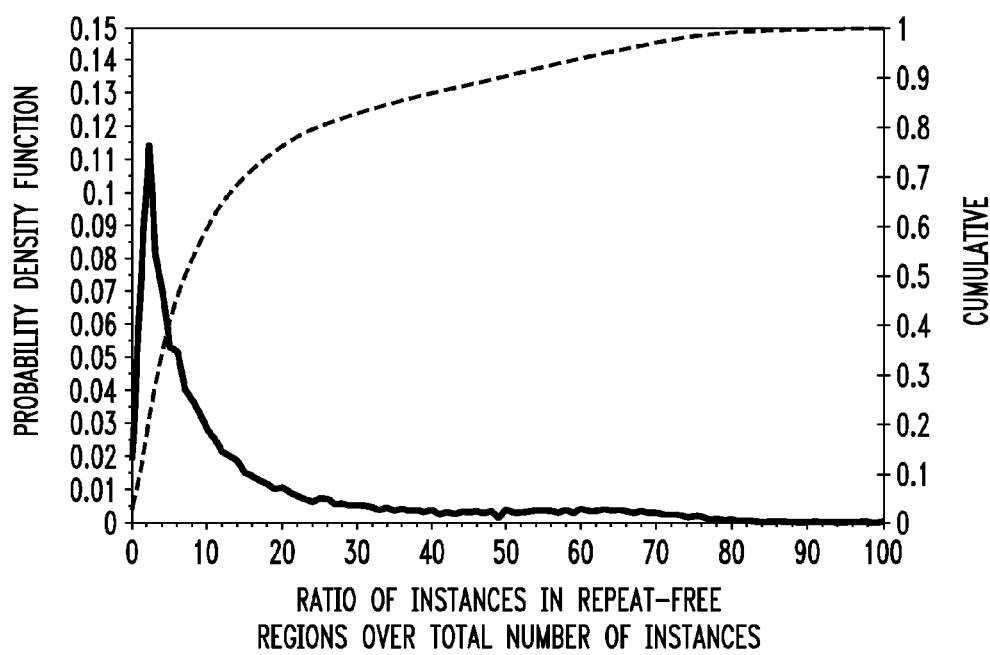
FIG. 14 is a diagram illustrating a probability density function and corresponding cumulative function for variable representing the fraction of pyknon instances located in repeat-free regions, according to an embodiment of the present invention.

On pyknons and repeat elements. 1,292 pyknons (1.0%) have instances occurring exclusively inside repeat elements as determined with the help of RepeatMasker (Smit, A. & Green, P. RepeatMasker: ftp.genome.washington.edu/RM/RepeatMasker.html). Seventy-nine pyknons have instances exclusively in repeat-free regions. And, the remaining 126,627 pyknons (98.9% of total) have instances both inside repeat elements and in repeat-free regions. A question that arises here is what fraction, on average, of the total number of copies of pyknons is generated from repeat-free regions. We have computed the probability density and cumulative functions for this fraction, and plot them in FIG. 14. As can be seen, about 60% of the pyknons have more than 90% of their copies inside repeat elements. However, the remaining 40% of the pyknons, which amounts to a little more than 50,000 pyknons, have between 10% and 100% of their instances in regions that are free of repeats.

The pyknons are distinct from the "ultraconserved elements." 52 pyknons have instances in 46 of the 481 ultraconserved elements (Bejerano, G., Pheasant, M., Makunin, I., Stephen, S., Kent, W. J., Mattick, J. S. & Haussler, D. (2004) *Science* 304, 1321-5) and cover 0.67% of the 126,007 positions: uc.73+ contains four pyknons; uc.23+, uc.66+, uc.143+ and uc.414+ each contain two pyknons; the remaining 41 elements contain a single pyknon each.

The pyknons are associated with specific biological processes. For 663 GO terms (Ashburner, M., Ball, C. A., Blake, J. A., Botstein, D., Butler, H., Cherry, J. M., Davis, A. P., Dolinski, K., Dwight, S. S., Eppig, J. T., Harris, M. A., Hill, D. P., Issel-Tarver, L., Kasarskis, A., Lewis, S., Matese, J. C., Richardson, J. E., Ringwald, M., Rubin, G. M. & Sherlock, G. (2000) *Nat Genet* 25, 25-9) describing biological processes at varying levels of detail, we found that the corresponding genes had either a significant enrichment or a significant depletion in pyknon instances. FIG. 15 shows a partial list of GO terms that are enriched or depleted in pyknons. We determined these associations as follows: each gene was included in a list n times, where n is the number of pyknons found in its 5' untranslated, coding or 3' untranslated region, respectively—to avoid over-counting, pyknons with multiple instances in the transcript(s) of a given gene were counted only once. For the sets of sequences belonging to human 5'UTRs, CRs and 3'UTRs, respectively, the binomial distribution was used to estimate the significance of enrichment (or depletion) of pyknons encountered in a group of genes associated with a certain term, compared to the expected frequency of this term in a background set comprising all genes with 5' untranslated, coding or 3' untranslated regions respectively.

Two control tests helped ensure the significance of our findings. First, we generated gene lists identical to the ones derived from the real data but which were created by random associations with pyknons: we found that only 1 of the generated 84,780 p-values exceeded our selected significance threshold of a Bonferroni-corrected|log(p-value)|of about 2.3 (data not shown). Second, we examined the relation between GO-process associations and the amount of sequence covered by the pyknons: this test allowed us to rule out the possibility that the derived significant enrichment/depletion were due to variations in sequence length for the genes associated with given cellular processes.

Figure 16:
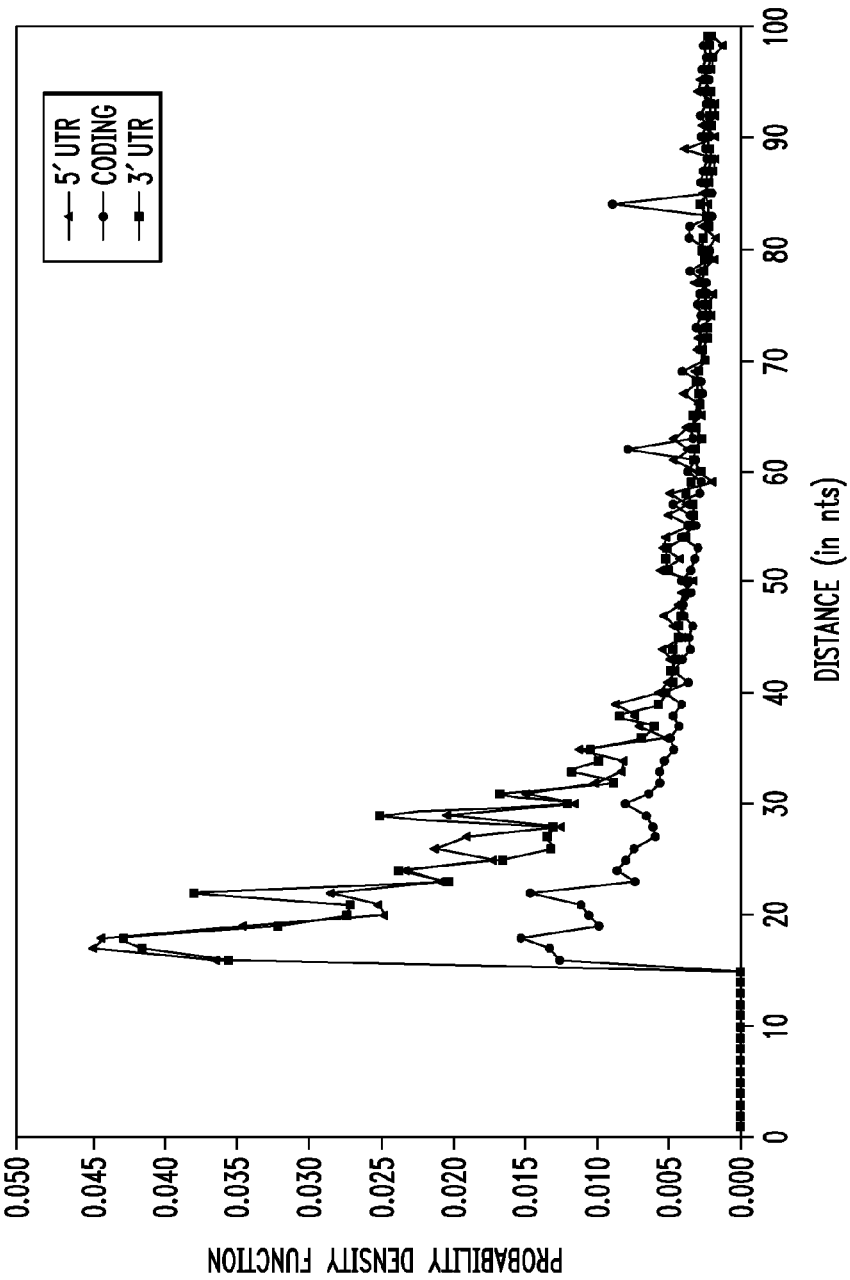
FIG. 16 is a diagram illustrating probability density functions for the distance between starting points of consecutive instances of pyknons, according to an embodiment of the present invention.

The relative positioning of pyknons in 5'UTRs, CRs and 3'UTRs is strongly biased but consecutive pyknon instances are not correlated. We examined the distances between consecutive pyknons, independently for each of the 5'UTRs, CRs and 3'UTRs. FIG. 16 shows the calculated probability density functions. Given the stringent criteria, we used when selecting pyknons, the coverage of each region is not dense, hence the tail-heavy distributions. The three curves have similar shapes, pronounced peaks at abscissas 18 and 22, and an overall preference for distances between 18 and 31 nucleotides.

Figure 17A:
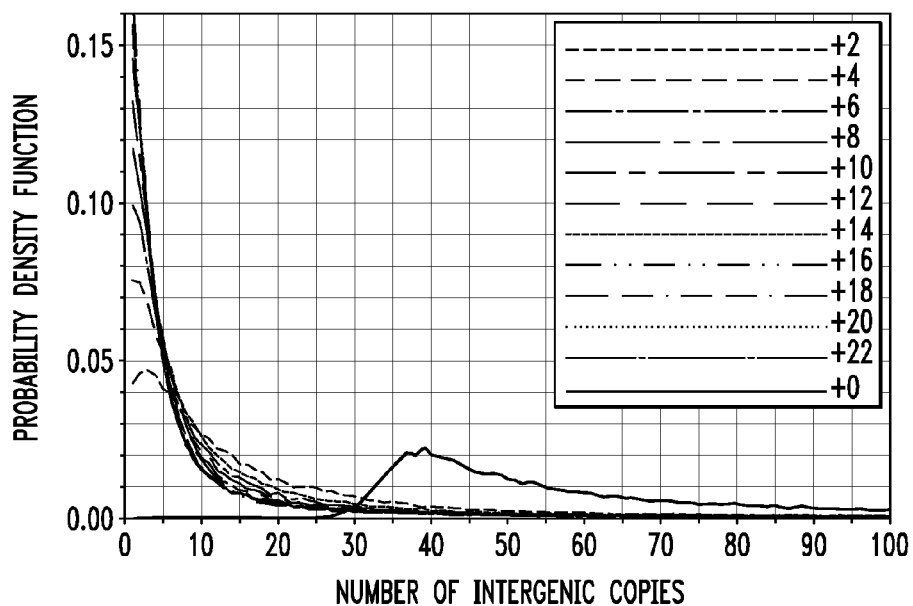
FIG. 17 is a diagram illustrating probability density functions for the number of intergenic and intronic copies of variable-length strings derived by counting instances of 3'UTR-conserved pyknons after shifting, according to an embodiment of the present invention.
Figure 17B:
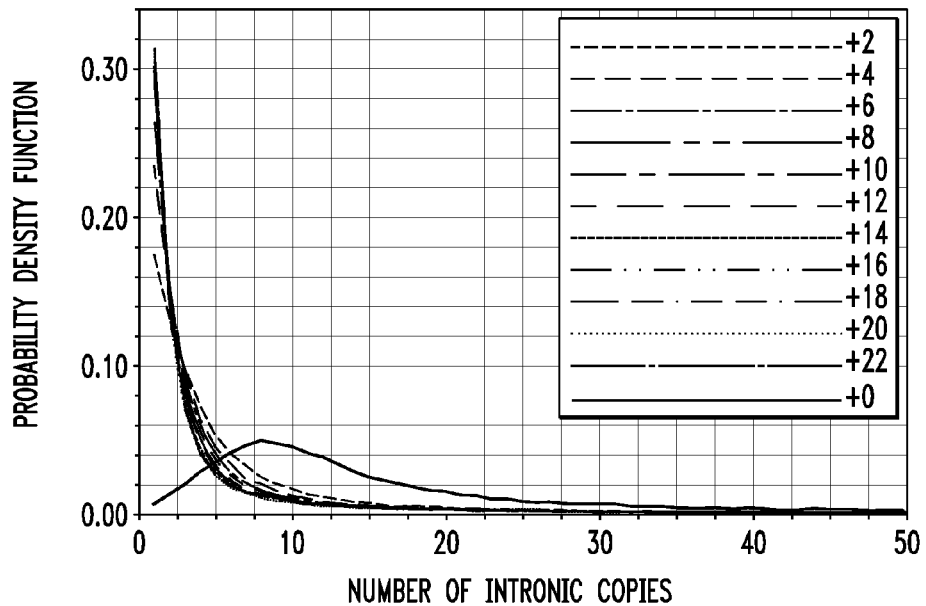

We next examined whether or not the pyknons are fragments of larger conserved regions. Let b denote a pyknon and let us assume that, unbeknownst to us, b is part of a larger-size conserved unit B. Then B will correspond to a larger area than the instance carved out by b, and thus there will be length(B)−length(b)+1 strings in the immediate neighborhood of b whose intergenic and intronic counterparts have as many identically-conserved copies as b. We tested this possibility in 3'UTRs by taking each instance of a pyknon, shifting it by +d (resp. −d), generating a new string and locating the new string's instances in the human intergenic and intronic regions. Had b been part of a larger logical unit, then for some values of d the number of intergenic and intronic copies of the newly formed string would have remained identical to those of b. On the other hand, if b were not part of a larger unit, then the new string would now cross the "natural boundaries" of the underlying presumed logical units and the new string's intergenic/intronic copies would be reduced drastically. Given the strict criteria that we used in identifying pyknons, it is possible that we discarded blocks that are conserved in intergenic/intronic regions and have instances in human coding regions. In this case, a shift of +/−d may end up generating a string that was not included in our set of pyknons but continues to have numerous intergenic/intronic copies. FIG. 17 shows the results obtained for the 3'UTRs for d ∈ and separately for intergenic (top half) and intronic (bottom half) regions; the curves for d=0 correspond to the pyknons in $P_{3'UTR}$. Note that even for a small shift of d=2 positions, the derived, shifted strings have strikingly fewer copies than the pyknons in $P_{3'UTR}$, and this holds true for both the intergenic and intronic instances. We obtained similar results for negative d's (data not shown).

The pyknons are possibly linked to PTGS. The most conspicuous feature of FIG. 16 is the strong preference for distances typically encountered in the context of PTGS. By definition, the 127,998 pyknons have one or more instances in the untranslated and coding regions of human genes: for each pyknon, we generated its reverse complement $\bar{\beta}$, identified all of $\bar{\beta}$'s intergenic and intronic instances, and predicted the RNA structure and folding energy of the immediately surrounding neighborhoods using the Vienna package (Hofacker, I. L., Fontana, W., Stadler, P., Bonhoeffer, L. S., Tacker, M. & Schuster, P. (1994) *Monatshefte f Chemie* 125, 167-188). We discarded structures whose predicted folding energies were >−30 Kcal/mol, and structures (including ones with favorable folding energies) that were predicted to locally self-hybridize, even if the involved positions represented a miniscule fraction of the total length of the regions under consideration. We also discarded structures that contained either a single large bulge or many unmatched bases. Each of the surviving regions was predicted to fold into a hairpin-shaped RNA structure that had a straightforward arm-loop-arm architecture, contained very small bulges if any, and was energetically very stable. The analysis identified 380,084 non-overlapping regions predicted to form hairpin-shaped structures (298,197 in intergenic and 81,887 in intronic sequences). These 380,084 regions contained instances of the reverse complement of 37,421 pyknons (29.23% of total). In terms of length, the clear majority of these regions are between 60 and 80 nucleotides long.

FIG. 18 shows the density of the surviving regions per 10,000 nucleotides and for each chromosome separately. The density is reported for each chromosome and separately for the intergenic and intronic regions. Per unit length, there are more predicted hairpins in intronic rather than intergenic regions but the shear difference in the magnitude of these regions results in the intergenic regions contributing the bulk of the hairpins. Interestingly, the density of discovered hairpins is not constant across chromosomes: chromosomes 16, 17, 19 and 22 who are the most densely-packed in terms of predicted hairpins are also among the shortest in length. We emphasize that the average pyknon has length similar to that of a typical microRNA and that there is a straightforward sense-antisense relationship between segments of the 380,084 hairpins and the pyknons instances in human 5'UTRs/CRs/3'UTRs. Also note that the regions containing the 81,887 intronic hairpins will be transcribed: these regions account for 21,727 of the 37,421 pyknons that are linked to hairpins.

If pyknons are indeed connected to PTGS, then two hypotheses arise from FIG. 16: a) in addition to 3'UTRs, gene silencing is likely effected through the 5'UTRs and amino acid coding regions; and, b) RNAi products in animals likely form distinct quantized categories based on size and have preferences for lengths of 18, 22, 24, 26, 29, 30 and 31 nucleotides.

The pyknons relate to known microRNAs. We formed the union of the RFAM (Griffiths-Jones, S., Bateman, A., Marshall, M., Khanna, A. & Eddy, S. R. (2003) *Nucleic Acids Res* 31, 439-41) and pyknon collections, and clustered it with the above-described BLASTN-based scheme, using a threshold of pair-wise remaining sequence similarity of 70%; i.e., we allowed up to six mismatches in 22 nucleotides. When comparing two sequences A and B, we avoided over-counting by examining for redundancy the pairs (A,B) and (reverse-complement-of-A,B). In total, 1,087 known microRNAs clustered with 689 pyknons across 279 of the 32,994 formed clusters.

The pyknons relate to recently discovered 3'UTR motifs. We compared the pyknons in $P_{3'UTR}$ to the 72 8-mer motifs that were recently reported to be conserved in human, mouse, rat and dog 3'UTRs (Xie, X., Lu, J., Kulbokas, E. J., Golub, T. R., Mootha, V., Lindblad-Toh, K., Lander, E. S. & Kellis, M. (2005) *Nature* 434, 338-45). We say that one of these 8-mers coincides with a pyknon of length l if one of the following conditions holds: the 8-mer agrees with letters 1-7 through l of a pyknon ('type 0' agreement); the 8-mer agrees with letters 1-8 through l-1 ('type 1' agreement); or, the 8-mer agrees with letters 1-9 through l-2 ('type 2' agreement). Of the 72 reported conserved 8-mers, 39 were in 'type 0' agreement, 10 in 'type 1' agreement, and seven in 'type 2' agreement with one or more pyknons from $P_{3'UTR}$. Six of the 8-mers did not match at all any of the pyknons in $P_{3'UTR}$. In summary, the pyknons that we have derived by intragenomic analysis overlap with 56 out of the 72 motifs that were discovered through cross-species comparisons.

Human pyknons are also present in other genomes where they associate with similar biological processes. In FIG. 19, and for each of 7 genomes in turn, we show how many positions in region X of the genome at hand are covered by the human pyknons contained in set $P_X$, X={5'UTR,CODING, 3'UTR}. We account for length differences across genomes by reporting the number of covered positions per 10,000 nucleotides. FIG. 20 shows how many of the human pyknons contained in set $P_X$ can also be found in the region X of the genome under consideration, X={5'UTR,CODING,3'UTR}. FIG. 20 also shows the total number of intergenic and intronic positions covered by those of the human pyknons that are also in other genomes. Notably, the human genome contains more than 600 million nucleotides that are associated with identical copies of pyknons and are absent from the mouse and rat genomes. Interestingly, the human pyknons have many instances in the intergenic and intronic regions of the phylogenetically distant worm and fruit-fly genomes covering about 1.6 million nucleotides in each.

A set of 6,160 human-genome-derived pyknons are simultaneously present in human 3'UTRs (5,752 genes) and mouse 3'UTRs (4,905 genes) whereas a second set of 388 pyknons are simultaneously present in human 3'UTRs (565 genes), mouse 3'UTRs (673 genes) and fruit-fly 3'UTRs (554 genes). Strikingly, we found these two sets of common pyknons to be significantly over-represented in the same biological processes in these other genomes (i.e. mouse and fruit-fly) as in the human genome, even though the pyknons were initially discovered by processing the human genome in isolation (data not shown). The common processes include regulation of transcription, cell communication, signal transduction etc. Finally, for each of the 388 pyknons in this second set, we manually analyzed about 130 nucleotide-long neighborhoods centered on the instances of each pyknon across the human, mouse and fruit-fly 3'UTRs and for a total of more than 4,000 such neighborhoods: notably, we did not find any instance of syntenic conservation across the three genomes.

Accordingly, as explained above, we explored the existence of sequence-based links between coding and non-coding regions of the human genome and identified 127,998 pyknons with a combined 226,874 non-overlapping instances in the 5'UTRs, CRs or 3' UTRs of 30,675 transcripts from 20,059 human genes. In transcripts that contained multiple pyknon instances, we found that the pyknons arrange themselves combinatorially forming mosaics. Statistical analysis revealed that the untranslated and/or coding regions of genes associated with specific biological processes are significantly enriched/depleted in pyknons.

We also found that the pyknon placement in 5'UTRs, CRs and 3'UTRs is strongly biased: the starting positions of consecutive pyknons show a clear preference for distances between 18 and 31 nucleotides. Importantly, we found an apparent lack of correlation between consecutive pyknon instances in these regions. The observed bias in the relative placement of the pyknons is conspicuously reminiscent of lengths that are associated with small RNA molecules that induce PTGS, suggesting the hypothesis that the pyknons' instances correspond to binding sites for microRNAs. Analysis of the regions immediately surrounding the intergenic and intronic instances of the reverse complement of the 127,998 discovered pyknons revealed that 30.0% of the pyknons have instances within about 380,000 distinct, non-overlapping regions between 60 and 80 nucleotides in length that are predicted to fold into hairpin-shaped RNA secondary structures with folding energies $\leq -30$ Kcal/mol. Many of these predicted hairpin-shaped structures are located inside known introns and thus will be transcribed. Our analysis also suggests that PTGS may be effected though the genes' 5'UTR and amino acid regions, in addition to their 3'UTRs. Another resulting hypothesis is that RNAi products in animals likely fall into distinct categories that are quantized in terms of size and have preferences for lengths of 18, 22, 24, 26, 29, 30 and 31 nucleotides. Notably, through sequence-based analysis, we showed that about 40% of the known microRNAs are similar to 689 pyknons, and that the pyknons subsume 56 of the 72 recently reported 3'UTR motifs, lending further support to the possibility of a connection between the pyknons and RNAi/PTGS.

The intergenic/intronic copies of the 127,998 pyknons constrain approximately 900 million nucleotides of the human genome. Instances of human pyknons can also be found in other genomes namely C. elegans, D. melanogaster, G. gallus, M. musculus, R. norvegicus and C. familiaris. The number of human pyknons that can be located in the 5'UTRs, CRs and 3'UTRs of other genomes decreases with phylogenetic distance. Strikingly, the pyknons that we found inside mouse and fruit-fly 3'UTRs were over-represented in the same biological processes as in the human genome. On a related note, more than 600 million bases, which correspond to identically conserved intergenic and intronic copies of human pyknons, are not present in the mouse and rat genomes.

The fact that some of the intergenic/intronic copies of pyknons originate in repeat elements may lead one to assume that our analysis has merely 'rediscovered' such elements. However, as mentioned above, more than 50,000 of the pyknons have many of their instances in repeat-free regions. Moreover, the typical length of a pyknon is substantially smaller than, e.g., that of an ALU. It was recently reported that genes can achieve evolutionary novelty through the 'careful' incorporation of ALUs in their coding regions (Iwashita, S., Osada, N., Itoh, T., Sezaki, M., Oshima, K., Hashimoto, E., Kitagawa-Arita, Y., Takahashi, I., Masui, T., Hashimoto, K. & Makalowski, W. (2003) *Mol Biol Evol* 20, 1556-63; and Lev-Maor, G., Sorek, R., Shomron, N. & Ast, G. (2003) *Science* 300, 1288-91). Also, the "pack-mule" paradigm revealed that entire genes, large fragments from a single gene, or fragments from multiple genes can be 'hijacked' by transposable elements (Jiang, N., Bao, Z., Zhang, X., Eddy, S. R. & Wessler, S. R. (2004) *Nature* 431, 569-73). However, 'fortuitous coincidence' is generally considered the prevailing mechanism by which such potential is unleashed. Contrasting this, the combinatorial arrangement of the pyknons within the untranslated and coding regions of genes together with the large number of instances in these regions and the association of pyknons with specific biological processes suggests that their placement is not accidental and likely serves a specific purpose. Our findings do not rule out a link with transposable elements. On the contrary, the findings seem to support a dynamic view of a genome (Jorgensen, R. A. (2004) *Cold Spring Harb Symp Quant Biol* 69, 349-54) that has learned to respond, and likely continues to respond, to environmental challenges or "stress" in a controlled, organized manner.

Taken together, the results suggest the existence of an extensive link between the non-coding and gene-coding parts in animal genomes. It is conceivable that this link could be the result of integration into the genome of dsRNA-breakdown products. Since many genes are known to give rise to antisense transcripts, it is possible that these genes were at some point subjected to RNAi-mediated dsRNA breakdown which in turn gave rise to products about 20 nucleotides in length. The latter, through repeated integration, could have eventually given rise to the numerous intergenic and intronic copies of the pyknons that we have identified. However, this explanation would have to be reconciled with four of our findings. First, the pyknons have identically conserved copies in non-genic regions. Second, pyknons appear to favor a specific size and, in genic regions, a specific relative placement. Third, slight modification of the 3'UTR instances of the pyknons by either prepending or appending immediately neighboring positions results in new strings whose intergenic and intronic copies are markedly decreased. And fourth, we can discover human pyknons in other organisms such as the mouse and the fruit-fly where they exhibit a persistent enrichment within specific processes yet are not the result of syntenic conservation. It may well be that we are seeing traces of an organized, coordinated activity that involves nearly all known genes. The existence of a pyknon-based regulatory layer that is massive in scope and extent, originates in the non-coding part of the genome, operates through the genes' untranslated and coding regions, and, is likely linked to PTGS, is a tantalizing possibility. Moreover, the observed disparity in the number of intergenic/intronic positions covered by human pyknons in the human and the phylogenetically-close mouse/rat genomes suggests that pyknons and thus the presumed regulatory layer may be organism-specific to some degree ("pyknome"). Addressing such questions might eventually help explain the apparent lack of correlation between the number of amino-acid coding genes in an organism and the organism's apparent complexity.

In the above description, and in order to identify motifs that are present in both non-genic and genic regions, we proceeded by first carrying out pattern discovery in the intergenic and intronic regions of the human genome. Once those patterns were determined, we identified additional instances for them in the genic regions of the genome and in particular in the 5' untranslated, amino acid coding and 3' untranslated regions of the genes. In other words, the computational analysis flowed from the non-genic to the genic-regions. But there is nothing that inherently prevents us from carrying out the computation in the other direction, i.e., from the genic to the non-genic regions, although there is potential for a loss in sensitivity that might result in the identification of smaller sets of motifs linking non-genic with genic regions. One could carry out the genic/non-genic analysis in a number of ways. For example, one could use a pattern discovery method to process the full collection of 5' untranslated, amino acid coding and 3' untranslated regions (with the regions processed separately or together), identifying recurrent motifs contained therein, and finally establishing links with the non-genic regions of the genome by locating the intergenic and intronic copies for these motifs. Instead of working with the full length sequences of the genes' untranslated and coding regions, an alternative method would be to delineate areas of interest in these regions (effectively subselecting), analyzing those areas to derive motifs, and finally locating additional instances of these motifs in the non-genic parts of the genome. Such areas of interest could, for example, be known or putative microRNA binding sites. Alternatively, the areas of interest could be what, in our work on the problem of RNA interference, we refer to as "target islands." A detailed description of the work is described in the U.S. patent application identified as Ser. No. 11/351,821, filed on Feb. 10, 2006, and entitled "System and Method for Identification of MicroRNA Target Sites and Corresponding Targeting MicroRNA Sequences," the disclosure of which is incorporated herein.

Summarily, our approach for finding target islands (i.e. putative microRNA binding sites) is known as rna22 and proceeds as follows: it discovers statistically significant patterns that are contained in the sequences of known microRNAs, generates their reverse complement, identifies all the instances of these reverse-complement patterns in a region of interest (namely one of 5'UTRs, CRs or 3'UTRs) and finally reports groups of consecutive locations from the region of interest as long as they are 'hit' a minimum number of times by these patterns. Generally, the groups of consecutive locations that rna22 reports will be variable in length and may correspond to one or more binding sites: consequently, and so as to not loose generality, we have been referring to them as "target islands."

Let us assume that target islands are available for the region of interest. One could proceed by doing an all-against-all comparison of the target islands forming clusters. Any two target-islands that end up in the same cluster have the property that their corresponding sequences share a substantial portion of their extent, say a minimum of N locations. Initially, each target island is in its own cluster. There is always the possibility that the thresholds used in the various stages of the process are too stringent, thus resulting in the method to miss some target-islands that could have otherwise become members of some cluster c. In order to account for this, one could enhance the cluster-forming process as follows. Using the Clustal-W multiple alignment algorithm (Chenna, R., Sugawara, H., Koike, T., Lopez, R., Gibson, T. J., Higgins, D. G. & Thompson, J. D. (2003) *Nucleic Acids Res* 31, 3497-500), we could align the sequences in cluster c and extract the core region of the alignment, then use it to search the sequences of interest for instances of the core region that were skipped because of the employed thresholds. If a given cluster contains more than one core regions then it can be replaced by as many new clusters as the number of its distinct core regions. For each one of the formed clusters whose core region that resulted from the Clustal-W alignment of its members is at least N nucleotides in length, we report the region as a (genic) motif.

Optionally, one can discard core regions that exhibit low-complexity using the NSEG algorithm (Wootton, J. C. & Federhen, S. (1993) *Computers in Chemistry* 17, 149-163). These motifs are then sought in the corresponding genome's intergenic/intronic regions instances to establish links between coding and non-coding parts of the genome. Finally, it is clear that instead of clustering the target islands to determine motifs, one could simply use a pattern discovery approach and subselect among the reported patterns to keep only those that, for example, satisfy a minimum length requirement, or some other property.

Given the above description, a few points should be noted. First, it is clear that the method which we have described and the ensuing analysis is not specific to the human genome; in fact, it can be carried out separately in other eukaryotic genomes such as chimpanzee, mouse, rat, dog, chicken, fruitfly, worm, etc. It is expected that the resulting pyknomes will have non-zero intersections with one another but will likely also contain organism-specific pyknons. Whether generated from the human or some other genome, the pyknons are statistically significant and link the non-genic and genic regions of the genome at hand. The links that are instantiated by the pyknons are 'natural' in that they involve large numbers of sequences that occur naturally in the genome at hand. Consequently, the pyknons would form natural candidates for a number of processes that to date have been carried out using schemes that make use of local information alone and do not take into account long-range conservations of the kind that we presented in our discussion.

Figure 21:
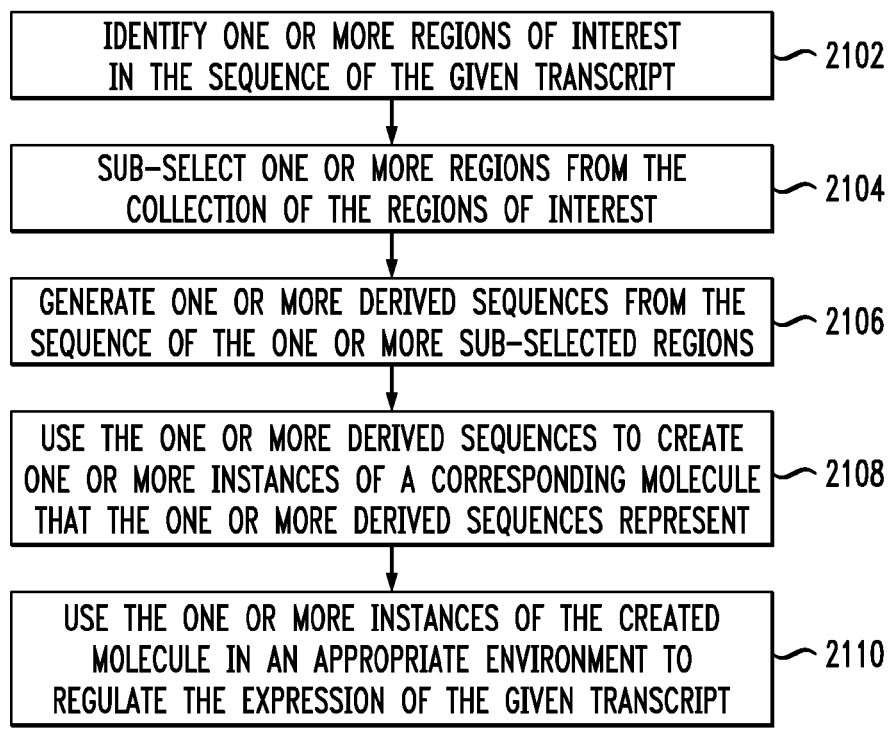
FIG. 21 is a diagram illustrating a first methodology for using pyknons, according to an embodiment of the present invention.

One such application would be the design of interfering RNA molecules to regulate the gene expression of one specific gene. Some of our pyknons have the property of being shared by two or more genes which allows the design of siRNAs that can interfere with a cluster of genes at once. In the flow diagram of FIG. 21, we illustrate a method for designing one or more sequences of interfering RNA molecules that can interact with one or more sites in a given transcript of a given sequence in a given organism and result in the down-regulation of the expression of the protein product encoded by the given transcript can comprise the following steps. One or more regions of interest are identified in the sequence of a given transcript (step 2102). One or more regions are sub-selected from the collection of these regions (step 2104). One or more derived sequences are generated from the sequence of the one or more sub-selected regions (step 2106). The one or more derived sequences are used to create one more instances of the corresponding molecule that the one or more derived sequences represent (step 2108). The one or more instances of the created molecule are used in an appropriate environment to regulate the expression of the given transcript (step 2110).

Further, the method of designing one or more interfering RNA molecules may use a region of interest in the collection of regions of interest identified to be an instance of a motif that has one or more copies in the intergenic and intronic regions of the genome of interest, and one or more copies in the untranslated and amino acid coding regions of one or more genes in the genome of interest, each such region of interest being computed using the method and system for finding pyknons described above.

The method may use a region of interest in the collection of regions of interest identified using a method that is based on pattern discovery, for example, the method described in the above-referenced U.S. patent application identified as Ser. No. 11/351,821. A region of interest in the collection of regions of interest can also be identified to be a target island that is computed using the method also described in the above-referenced U.S. patent application identified as Ser. No. 11/351,821.

The method of designing one or more interfering RNA molecules may also use a region of interest, for example, located in the 5' untranslated region of the given transcript, located in the amino acid coding region of the given transcript, or located in the 3' untranslated region of the given transcript.

As detailed above, the method of designing one or more interfering RNA molecules can be used where the genome of interest is a eukaryotic genome, and wherein the eukaryotic genome is, for example, the human genome, the mouse genome, the rat genome, the dog genome, the fruit fly genome, or the worm genome.

Also, the method of designing one or more interfering RNA molecules may use a region of interest that is sub-selected based on one or more of its attributes. These attributes may include, for example, the region's length and the region's location in the transcript.

The method of designing one or more interfering RNA molecules can also use a derived sequence that is, for example, the reverse complement of the sequence of the one or more sub-selected regions, or a near-reverse complement of the sequence of the one or more sub-selected regions, i.e. it contains mismatches at one or more locations.

The method of designing one or more interfering RNA molecules can be used such that the one or more copies of the molecule can be built using any of a set of biochemical processes.

Another application would involve the rational use of pyknons to appropriately engineer a transcript of interest in order to control its expression (either up-regulate or down-regulate) in a specific tissue or for a specific cellular process. For example, one could remove one or more of the pyknons existing in the transcript of interest leading to an up-regulation of the transcript. Alternatively, one could down-regulate the transcript of interest by adding more instances of existing pyknons and rely on the naturally occurring agent that targets this pyknon to induce down-regulation. Or one could add the sequence of a pyknon that is not among those contained in the transcript and selectively control the transcript's expression by adding or removing appropriately generated instances of the reverse complement of the pyknon.

Figure 22:
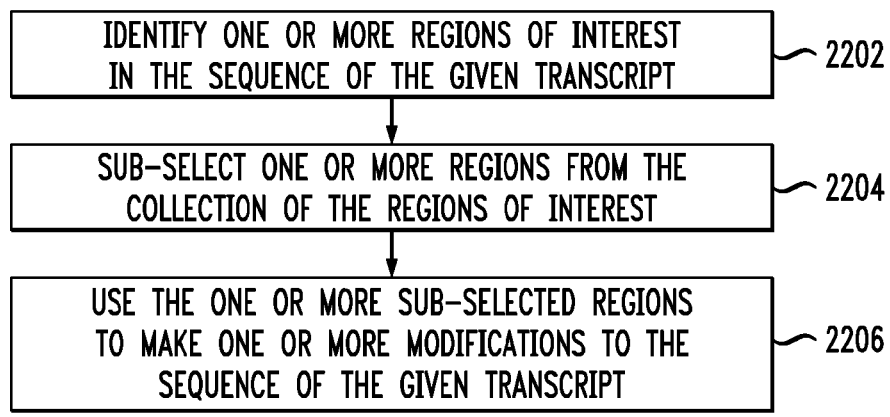
FIG. 22 is a diagram illustrating a second methodology for using pyknons, according to an embodiment of the present invention.

As illustrated in the flow diagram of FIG. 22, a method for engineering a given transcript of a given gene in a given organism in order to regulate its expression may comprise the following steps. One or more regions of interest are identified in the sequence of a given transcript (step 2202). One or more regions are sub-selected from the collection of these regions (step 2204). The one or more sub-selected regions are used to make one or more modifications to the sequence of the given transcript (step 2206).

Further, the method of engineering a given transcript to regulate gene expression can comprise many of the same steps as mentioned above in the method for designing one or more interfering RNA molecules. For example, the method of engineering a given transcript to regulate gene expression may use a region of interest in the collection of regions of interest identified to be an instance of a motif that has one or more copies in the intergenic and intronic regions of the genome of interest, and one or more copies in the untranslated and amino acid coding regions of one or more genes in the genome of interest. The motif can be computed, for example, using the pyknons discovery method and system described above.

Also, as above, the method of engineering a given transcript to regulate gene expression may use a region of interest in the collection of regions of interest computed using a method that is based on pattern discovery, for example, the method described in the above-referenced U.S. patent application identified as Ser. No. 11/351,821.

The present method may also use a region of interest, for example, located in the 5' untranslated region of the given transcript, located in the amino acid coding region of the given transcript, or located in the 3' untranslated region of the given transcript.

Also, similar to the above methodology, the method of engineering a given transcript to regulate gene expression may use a region of interest that is sub-selected based on one or more of its attributes including, for example, the region's length and the region's location in the transcript. Additional attributes may include the association of the region with a given biological process, the region's association with a given tissue, and the region's association with a given cellular compartment.

Further, the method of engineering a given transcript to regulate gene expression can include a modification that, for example, comprises an extension of the sequence of the given transcript, or a shortening of the sequence of the given transcript. The extension can, for example, comprise one or more instances of a region of interest, and the shortening can, for example, comprise one or more instances of a region of interest.

Another application of pyknons, for example, would be the measuring of the impact that one or more pyknons can have on a gene's regulation "by proxy." This would entail the engineering of an assay that involves a reporter gene (for example, luciferase) and instances of the one or more pyknons placed downstream from the region that codes for the reporter's amino acid sequence. Then, one can measure the impact on the expression of the reporter gene by using various combinations of appropriately generated instances of the reverse complement of these pyknons. The observations made in the context of the reporter assay can then be carried over to the gene that is studied. Additional applications are also possible if one assumes that for the organism that is being studied the sequences of the corresponding pyknons are available.

Figure 23:
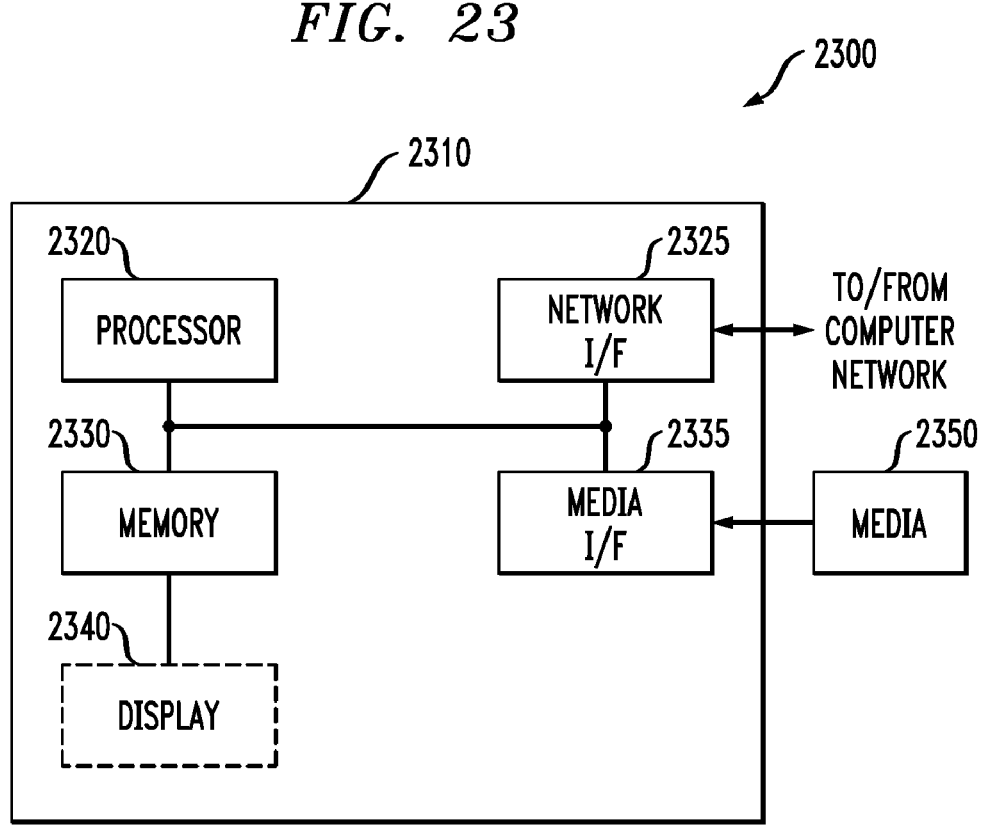
FIG. 23 is a block diagram of an exemplary hardware implementation of one or more of the methodologies of the present invention, according to an embodiment of the present invention.

FIG. 23 is a block diagram of an exemplary hardware implementation of one or more of the methodologies of the present invention. That is, apparatus 2300 may implement one or more of the steps/components described above in the context of FIGS. 1-22. Apparatus 2300 comprises a computer system 2310 that interacts with media 2350. Computer system 2310 comprises a processor 2320, a network interface 2325, a memory 2330, a media interface 2335 and an optional display 2340. Network interface 2325 allows computer system 2310 to connect to a network, while media interface 2335 allows computer system 2310 to interact with media 2350, such as a Digital Versatile Disk (DVD) or a hard drive.

As is known in the art, the methods and apparatus discussed herein may be distributed as an article of manufacture that itself comprises a computer-readable medium having computer-readable code means embodied thereon. The computer-readable program code means is operable, in conjunction with a computer system such as computer system 2310, to carry out all or some of the steps to perform one or more of the methods or create the apparatus discussed herein. For example, the computer-readable code is configured to implement a method of determining associations between non-coding sequences and gene coding sequences in a genome of an organism, by the steps of: identifying at least one conserved region from a plurality of the non-coding sequences; and linking the at least one conserved region with one or more of the gene coding sequences of the genome to associate the at least one conserved region with one or more biological processes of the organism. The computer-readable medium may be a recordable medium (e.g., floppy disks, hard drive, optical disks such as a DVD, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used. The computer-readable code means is any mechanism for allowing a computer to read instructions and data, such as magnetic variations on a magnetic medium or height variations on the surface of a compact disk.

Memory 2330 configures the processor 2320 to implement the methods, steps, and functions disclosed herein. The memory 2330 could be distributed or local and the processor 2320 could be distributed or singular. The memory 2330 could be implemented as an electrical, magnetic or optical memory, or any combination of these or other types of storage devices. Moreover, the term "memory" should be construed broadly enough to encompass any information able to be read from or written to an address in the addressable space accessed by processor 2320. With this definition, information on a network, accessible through network interface 2325, is still within memory 2330 because the processor 2320 can retrieve the information from the network. It should be noted that each distributed processor that makes up processor 2320 generally contains its own addressable memory space. It should also be noted that some or all of computer system 2310 can be incorporated into an application-specific or general-use integrated circuit.

Optional video display 2340 is any type of video display suitable for interacting with a human user of apparatus 2300. Generally, video display 2440 is a computer monitor or other similar video display.

Pattern-discovery techniques, such as those described above, have been used in conjunction with recently released, publicly available genomic sequences to predict pyknons related to the following organisms: *C. elegans* (Wormbase release 150); *D. melanogaster* (Berkely *Drosophila* Genome Project release 4); *G. gallus* (Washington University in St. Louis release 1.0); *M. musculus* (Ensembl assembly based on the NCBI 34 assembly); *R. norvegicus* (Genome assembly RGSC3.4); *C. familiaris* (Genome assembly BROADD1); *P. troglodytes* (Genome assembly CHIMP1A); and *H. sapiens* (Ensembl assembly based on the NCBI 31 assembly). Namely, pyknon sequences having SEQ ID NO: 1 through SEQ ID NO: 180,269 derived from the genome of *H. sapiens* are presented; pyknon sequences having SEQ ID NO: 180,270 through SEQ ID NO: 295,005 derived from the genome of *P. troglodytes* are presented; pyknon sequences having SEQ ID NO: 295,006 through SEQ ID NO: 335,709 derived from the genome of *C. familiaris* are presented; pyknon sequences having SEQ ID NO: 335,710 through SEQ ID NO: 463,044 derived from the genome of *M. musculus* are presented; pyknon sequences having SEQ ID NO: 463,045 through SEQ ID NO: 534,157 derived from the genome of *R. norvegicus* are presented; pyknon sequences having SEQ ID NO: 534,158 through SEQ ID NO: 541,832 derived from the genome of *G. gallus* are presented; pyknon sequences having SEQ ID NO: 541,833 through SEQ ID NO: 682,206 derived from the genome of *D. melanogaster* are presented; and, pyknon sequences having SEQ ID NO: 682,207 through SEQ ID NO: 747,326 derived from the genome of *C. elegans* are presented. While the pattern discovery embodiments described herein are preferred methods, alternatives and variations can also be used to predict pyknons.

The predicted pyknon sequences generated using the pattern discovery techniques described herein are submitted herewith in electronic text format as the file 1500-696 Complete Sequence Listing.ST25, created on Monday Nov. 20, 2006, having a size of 109 Megabytes on compact disc, the contents of which are incorporated by reference herein. Two identical copies of the sequences are submitted herewith.

With respect to the sequences submitted herewith, each pyknon sequence is listed and numbered consecutively, and the organism from which the sequence was derived is also identified.

All of the sequences presented herein, SEQ ID NO: 1 through SEQ ID NO: 747,326 are listed as DNA sequences. RNA transcripts corresponding to these DNA sequences can also be derived for use with the present invention. As such, the RNA forms of these DNA sequences are considered to be within the scope of the present teachings.

Sequences that are either homologous or orthologous to the sequences presented herein, e.g., sequences that are related by vertical descent from a common ancestor or through other means (e.g., through horizontal gene transfer), will likely be present in genomes other than the ones mentioned herein. Such homologous/orthologous sequences are expected to generally differ from the sequences listed herein at only a small fraction of the locations. Thus, the teachings presented herein should be construed as being broadly applicable to such homologous/orthologous sequences from species other from those listed above.

Furthermore, sequences that are derived from the sequences presented herein through appending or prepending a small number of nucleotides to the presented sequences should also be considered to fall under the teachings presented herein. Sequences that are derived by taking the reverse complement of the sequences presented herein should also be considered to fall under the teachings presented herein.

According to an exemplary embodiment, interfering RNA molecules may be generated based on the sequences of the predicted pyknon sequences. These interfering molecules may be generated so that they target for repression (post-transcriptional silencing activity) transcripts (both naturally occurring sequences as well as designed constructs) that contain one or more of the pyknon sequences described herein, i.e. they target the area of the transcript that corresponds to an instance of a pyknon from the collection of pyknons described herein.

Alternatively, an interfering RNA molecule can be generated from the reverse complement of the pyknon sequences described herein. In this case, the interfering RNA molecule will target for repression transcripts that contain an instance of a pyknon from the collection of pyknons described herein or a sequence only slightly different from the sequence of the considered pyknon. The RNA molecules generated in this manner may then be used to regulate gene expression by inducing post-transcriptional silencing of the gene. Also, pyknon sequences can be used to derive an inducer of post-transcriptional silencing activity, wherein the sequence of the inducer is derived by taking the reverse complement of at least one of one or more pyknon sequences. Using the predicted pyknon sequences to study or affect gene expression may be conducted using techniques and procedures commonly known to those skilled in the art.

In accordance with the embodiments detailed above, the expression of a transcript can be regulated by using at least one nucleic acid molecule that binds to an area of said transcript that corresponds to at least one of one or more pyknon sequences having SEQ ID NO: 1 through SEQ ID NO: 747,326. Also, the expression of a transcript can be regulated by using at least one interfering RNA molecule that contains a region that corresponds to the reverse complement of at least one of one or more pyknon sequences having SEQ ID NO: 1 through SEQ ID NO: 747,326.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08178503B2). An electronic copy of the "Sequence Listing" will also be available from the USPTO upon request and payment of the fee set forth in 37 CFR 1.19(b)(3).

What is claimed is:

1. A method for decreasing the expression of a transcript, the method comprising the steps of:
    identifying one or more regions of interest in a sequence of the given transcript;
    sub-selecting, within the one or more identified regions of interest, a motif, wherein sub-selecting a motif comprises identifying one or more identically conserved copies of the motif in intergenic and intronic regions of a genome of interest for the given transcript and identifying one or more additional copies in untranslated and amino acid coding regions of one or more genes in the genome of interest, wherein sub-selecting a motif further comprises using a pattern discovery technique with a pre-determined parameter of minimum size of discovered pattern and a pre-determined parameter of minimum required number of discovered copies before a pattern can be deemed as identified;
    generating one or more derived sequences from the sub-selected motif;
    creating, from the one or more derived sequences, at least one instance of the corresponding molecule that the one or more derived sequences represent, wherein the at least one instance of the corresponding molecule comprises at least one interfering RNA molecule; and
    using the at least one interfering RNA molecule to decrease the expression of the given transcript.

* * * * *